US00RE48039E

(19) United States
(12) Reissued Patent
Swanson

(10) Patent Number: US RE48,039 E
(45) Date of Reissued Patent: Jun. 9, 2020

(54) STIMULATION PROSTHESIS WITH CONFIGURABLE DATA LINK

(71) Applicant: COCHLEAR LIMITED, Macquarie University, NSW (AU)

(72) Inventor: Brett Swanson, St. Ives (AU)

(73) Assignee: Cochlear Limited, Macquarie University, NSW (AU)

(21) Appl. No.: 15/818,085

(22) Filed: Nov. 20, 2017

Related U.S. Patent Documents

Reissue of:
(64) Patent No.: 9,216,288
Issued: Dec. 22, 2015
Appl. No.: 13/334,322
Filed: Dec. 22, 2011

(51) Int. Cl.
*A61F 11/04* (2006.01)
*A61N 1/36* (2006.01)
*A61N 1/372* (2006.01)
*H04R 25/00* (2006.01)

(52) U.S. Cl.
CPC ..... *A61N 1/36032* (2013.01); *A61N 1/3727* (2013.01); *H04R 25/505* (2013.01); *H04R 25/606* (2013.01)

(58) Field of Classification Search
CPC ..... A61N 1/3727; A61N 1/36032; A61N 1/36036; A61N 1/36; A61N 1/372; H04R 25/606; H04R 25/505; A61F 11/04; A61F 11/045
See application file for complete search history.

(56) References Cited

U.S. PATENT DOCUMENTS 4,532,930 A * 8/1985 Crosby ..... A61N 1/36036 607/57
4,793,353 A * 12/1988 Borkan ..... 607/60
5,597,380 A 1/1997 McDermott
5,603,726 A 2/1997 Schulman et al.
5,741,314 A 4/1998 Daly ..... A61N 1/37223 128/903
5,876,425 A * 3/1999 Gord ..... A61N 1/36185 607/33
6,219,580 B1 4/2001 Faltys
(Continued)

OTHER PUBLICATIONS

International Search Report and Written Opinion for International Application No. PCT/IB2012/057496, dated May 30, 2013.
(Continued)

*Primary Examiner* — Robert L Nasser
(74) *Attorney, Agent, or Firm* — Edell, Shapiro & Finnan, LLC

(57) ABSTRACT

The present application discloses systems and methods for operating a stimulation prosthesis that contains a command module and a stimulator module that communicate by a data link. The stimulation prosthesis has at least two operating states: a configuration state and a stimulation state. In one embodiment, the stimulation prosthesis may use a communication protocol that is suitable for the current operating state. The risk of unintended transitions between the operating states due to data transmission errors is substantially eliminated. And in accordance with another embodiment, in addition to switching stimulation strategies, the stimulation prosthesis may also switch stimulation data formats to a format that is optimized for the new stimulation strategy.

25 Claims, 18 Drawing Sheets

(56) References Cited

U.S. PATENT DOCUMENTS

| | | | | |
|---|---|---|---|---|
| 6,594,525 | B1 | 7/2003 | Zierhofer | |
| 6,600,955 | B1 | 7/2003 | Zierhofer | |
| 7,072,717 | B1 | 7/2006 | Wolf | |
| 7,310,558 | B2 | 12/2007 | Van Hoesel | |
| 7,860,573 | B2 * | 12/2010 | van den Honert | A61N 1/0541 607/57 |
| 8,509,908 | B2 * | 8/2013 | Van Assche | A61N 1/37211 607/59 |
| 2004/0138711 | A1 * | 7/2004 | Osorio et al. | 607/3 |
| 2005/0129262 | A1 | 6/2005 | Dillon et al. | |
| 2009/0024184 | A1 * | 1/2009 | Sun | A61N 1/36038 607/57 |
| 2009/0157143 | A1 | 6/2009 | Edler et al. | |
| 2009/0252357 | A1 | 10/2009 | Komagel et al. | |
| 2010/0128906 | A1 | 5/2010 | Haenggi et al. | |
| 2010/0204756 | A1 * | 8/2010 | Aghassian | A61N 1/37223 607/60 |
| 2013/0090517 | A1 * | 4/2013 | Van den Heuvel | A61N 1/37264 600/25 |
| 2013/0268024 | A1 * | 10/2013 | Goddeeris | A61N 1/37252 607/57 |
| 2014/0275730 | A1 * | 9/2014 | Lievens | H04R 25/606 600/25 |

OTHER PUBLICATIONS

Wilson et al., Better SPeech Recognition with Cochlear Implants, Letter to Nature, Jul. 1991, vol. 352 at 236-38.

* cited by examiner

Program Code 900

```
Rx_command:
    # Receive entire frame before testing value.
    c = rx(5)
    b = rx(8)
    fe = 0                      # Because we do not reply to non-header frames,
                                # need to explicitly clear frame error.
    a = HEADER_W5
    a -= c
    if a != 0 goto Rx_command   # Did not match.

    a = HEADER_W8
    a -= b
    if a != 0 goto Rx_command   # Did not match.

    a = IMPLANT_TYPE
    tx_a(2)                     # Reply with implant type code.

    e = 0                       # Clear frame counter
    call Rx_frame_count
    a = rx(8)                   # Rx address of routine to be executed.
    call_a                      # Call specified routine.
    goto Rx_command



Bad_frame:
    a = e                       # frame count
    tx_a(2)                     # Tx unchanged expected frame count (LSBs).
    a = rx(8)                   # Rx data (8 bits) and discard.



Rx_frame_count:
    a = rx(5)                   # Rx count.
    if fe goto Bad_frame
    a -= e                      # Compare received count to frame count.
    if a != 0 goto Bad_frame
    a = 0x1f                    # maximum 5-bit value
    a -= e                      # Check for wrap-around.
    if a == 0 goto Save
    a = 1
    a += e                      # a = frame_count + 1

Save:
    e = a                       # frame_count = a
    tx_a(2)                     # Tx next expected frame count (LSBs).
    return                      # Ready to rx 8-bit data.
```

FIG. 9

Program Code 1000

```
Load_mem:
    call Rx_frame_count
    b = rx(8)                    # Rx bank
    call Rx_frame_count
    c = rx(8)                    # Rx channel
    call Rx_frame_count
    d = rx(8)                    # Rx number of words
Load_mem_loop:
    call Rx_frame_count
    a = rx(8)                    # Rx data byte
    m[bc] = a                    # Store data byte
    c++
    if --d goto Load_mem_loop
    return
```

FIG. 10

Program Code 1100

```
Check_header:
    a = rx(num_extra_bits)          # Receive header bits
    d = expected_header
    a -= d
    if a == 0 goto End_header_check
    fe = 1                          # Subsequent rx bits will be 0
End_header_check:
```

FIG. 11

| frame 1 | |
|---|---|
| channel | amplitude |
| 5 | 8 |

FIG. 12A

| frame 1 | | frame 2 | | frame 3 | | frame 4 | | frame 5 | | frame 6 | |
|---|---|---|---|---|---|---|---|---|---|---|---|
| chan 1 | amplitude 1 | chan 2 | amplitude 2 | chan 3 | amplitude 3 | chan 4 | amplitude 4 | chan 5 | amplitude 5 | chan 6 | amplitude 6 |
| 5 | 8 | 5 | 8 | 5 | 8 | 5 | 8 | 5 | 8 | 5 | 8 |

FIG. 12B

| frame 1 | | | frame 2 | | frame 3 | | frame 4 | | frame 5 | |
|---|---|---|---|---|---|---|---|---|---|---|
| x | amplitude 1 | amplitude 2 | amplitude 3 | amplitude 4 | amplitude 5 | amplitude 6 | amplitude 7 | amplitude 8 | | |
| 1 | 8 | 8 | 8 | 8 | 8 | 8 | 8 | 8 | | |

FIG. 12C

| frame 1 | | | frame 2 | | frame 3 | | frame 4 | | frame 5 | | frame 6 | | frame 7 | | | |
|---|---|---|---|---|---|---|---|---|---|---|---|---|---|---|---|---|
| x | chan 1 | height 1 | chan 2 | height 2 | chan 3 | height 3 | chan 4 | height 4 | chan 5 | height 5 | chan 6 | height 6 | chan 7 | height 7 | chan 8 | height 8 |
| 3 | 5 | 6 | 5 | 6 | 5 | 6 | 5 | 6 | 5 | 6 | 5 | 6 | 5 | 6 | 5 | 6 |

FIG. 12D

| frame 1 | | | frame 2 | | frame 3 | | frame 4 | |
|---|---|---|---|---|---|---|---|---|
| x | height 1 | height 2 | height 3 | height 4 | height 5 | height 6 | height 7 | height 8 |
| 4 | 6 | 6 | 6 | 6 | 6 | 6 | 6 | 6 |

FIG. 12E

| frame 1 | frame 2 | frame 3 | | frame 4 | | frame 5 | | | frame 6 | |
|---|---|---|---|---|---|---|---|---|---|---|
| x | channel_flags | height 1 | height 2 | height 3 | height 4 | height 5 | height 6 | height 7 | height 8 | height 9 |
| 2 | 22 | 6 | 6 | 6 | 6 | 6 | 6 | 6 | 6 | 6 |

FIG. 12F

| | | | | | | | | | | |
|---|---|---|---|---|---|---|---|---|---|---|
| 11 | 0011011000000011011100 | 000110 | 101011 | 101000 | 111111 | 001000 | 100010 | 000011 | 111000 | 001010 |
| | | 6 | 43 | 40 | 63 | 8 | 34 | 3 | 56 | 10 height |
| | | 2 | 3 | 5 | 6 | 13 | 14 | 16 | 17 | 18 channel |

FIG. 12G

Program Code 1301

```
Stim_chan_amp:
    c = rx(5)                   # Receive channel number.
    a = rx(8)                   # Receive amplitude.
    pulse                       # Produce stimulation pulse.
    ack                         # Send reply to External processor.
    goto Stim_chan_amp          # Next packet.
```

FIG. 13A

Program Code 1302

```
Stim_chan_amp_group:
    d = num_pulses
Loop:
    c = rx(5)                   # Receive channel number.
    a = rx(8)                   # Receive amplitude.
    pulse                       # Produce stimulation pulse.
    if --d goto Loop
    ack                         # Send reply to External processor.
    goto Stim_chan_amp_group    # Next packet
```

FIG. 13B

Program Code 1303

```
Initial_delay:
    wait
    ack
Stim_amp_vector:
    a = rx(num_extra_bits)          # Receive header bits
    d = expected_header
    a -= d
    if a == 0 goto End_header_check
    fe = 1                          # Subsequent rx bits will be 0
End_header_check:
    c = 0
    d = num_channels
Loop:
    a = rx(num_bits_amplitude)      # Receive amplitude.
    pulse
    c++                             # Next channel.
    if --d goto Loop
    ack

    goto Stim_amp_vector            # Next packet.
```

FIG. 13C

Program Code 1304

```
Stim_chan_height:
    b = b_lower_level                # Point to lower_level table.
    d = num_pulses                   # Number of pulses per packet.
Loop:
    c = rx(num_bits_channel)         # Receive channel number.
    a = rx(num_bits_height)          # Receive height.
    a += m[bc]                       # Add lower_level.
    pulse
    if --d goto Loop

    ack
    goto Stim_chan_height            # Next packet.
```

FIG. 13D

Program Code 1305

```
Stim_height_vector:
    b = b_lower_level                # Point to lower_level table.
    c = 0
    d = num_channels
Loop:
    a = rx(num_bits_height)          # Receive height.
    a += m[bc]                       # amp = height + lower_level.
    pulse
    c++                              # Next channel.
    if --d goto Loop

    ack
    goto Stim_height_vector          # Next packet.
```

FIG. 13E

Program Code 1306

```
Stim_bit_mask_height:
Packet:
    b = b_bit_flag
    c = 0
    d = num_channels
    e = 0                        # counter for number of bit-flags received.
Loop_bit_flag:                   # Receive bit-flags and write to memory:
    a = rx(1)                    # a = flag.
    m[bc] = a                    # Store flag.
    a += e                       # Count flags.
    e = a
    c++                          # Next channel.
    if --d goto Loop_bit_flag
    c = 0                        # Needed for both sides of branch.
    a = num_pulses
    a -= e                       # Compare to number of bit-flags received.
    if a != 0 goto Bit_flag_error
    d = num_channels
Loop_pulse:                      # Receive amplitudes and output pulses:
    b = b_bit_flag               # Point to bit-flag
    a = m[bc]                    # Is channel selected?
    if a == 0 goto Next_channel # If not selected, skip channel.
    a = rx(num_bits_height)      # Receive height
    b = b_lower_level            # Point to lower_level
    a += m[bc]                   # amp = height + lower_level
    pulse
Next_channel:
    c++
    if --d goto Loop_pulse
    ack
    goto Packet                  # Next packet.

Bit_flag_error:
    d = num_pulses
    b = b_lower_level            # Point to lower_level.
Loop_min_pulse:
    a = rx(num_bits_height)      # Receive and discard.
    a = m[bc]
    pulse                        # Pulse at lower_level to maintain pulse timing.
    c++
    if --d goto Loop_min_pulse
    fe = 1                       # Set frame error, so that ack indicates error.
    ack
    goto Packet                  # Next packet.
```

FIG. 13F

Program Code 1700

```
Stim_interpolate_vector:
# Receive new heights, output interpolated amplitudes:
    c = 0
    d = num_channels
Loop_rx_and_interpolate:
    a = rx(num_bits_height)         # Receive new height.
    b = b_lower_level
    a += m[bc]                      # Add lower_level.
    b = b_latest_amplitude
    m[bc] = a                       # Store latest amplitude.
    b = b_previous_amplitude
    a += m[bc]                      # Add previous amplitude.
    a /= 2                          # Mean of latest & previous amplitudes.
    pulse                           # Output interpolated amplitude.
    c++                             # Next channel.
    if --d goto Loop_rx_and_interpolate

# Output latest amplitudes:
    c = 0
    d = num_channels
Loop_output_latest:
    b = b_latest_amplitude
    a = m[bc]                       # Retrieve latest amplitude.
    b = b_previous_amplitude
    m[bc] = a                       # Store as previous amplitude.
    pulse                           # Output latest amplitude.
    c++                             # Next channel.
    if --d goto Loop_output_latest

    ack
    goto Stim_interpolate_vector    # Next packet.
```

FIG. 17

Program Code 1800

```
Stim_height_vector_conditioner:
    a = num_conditioners
    e = a                        # Outer loop counter.
    b = b_conditioner_level      # Point to conditioner_level table.
Loop_conditioner_scan:
    c = 0
    d = num_channels
Loop_conditioner_pulse:
    a = m[bc]                    # amp = conditioner_level.
    pulse
    c++                          # Next channel.
    if --d goto Loop_conditioner_pulse
    if --e goto Loop_conditioner_scan
    b = b_lower_level            # Point to lower_level table.
    c = 0
    d = num_channels
Loop_information_pulse:
    a = rx(num_bits_height)      # Receive height.
    a += m[bc]                   # amp = height + lower_level.
    pulse
    c++                          # Next channel.
    if --d goto Loop_information_pulse

    ack
    goto Stim_height_vector_conditioner # Next packet.
```

FIG. 18

STIMULATION PROSTHESIS WITH CONFIGURABLE DATA LINK

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND

Various types of hearing prostheses may provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing aids. An acoustic hearing aid typically includes a small microphone to detect sound, an amplifier to amplify certain portions of the detected sound, and a small speaker to transmit the amplified sounds into the person's ear. Vibration-based hearing aids typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing aids may include bone anchored hearing aids, direct acoustic cochlear stimulation devices, or other vibration-based devices. A bone anchored hearing aid typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing aids may use similar vibration mechanisms to transmit sound via direct vibration of teeth or other cranial or facial bones.

Persons with certain forms of sensorineural hearing loss may benefit from cochlear implants and/or auditory brainstem implants. For example, cochlear implants may provide a person having sensorineural hearing loss with the ability to perceive sound by stimulating the person's auditory nerve via an array of electrodes implanted in the person's cochlea. FIG. 1 depicts an example cochlear implant. The example cochlear implant includes an external sound processor 101, which is typically worn behind the ear. The cochlear implant has at least one microphone 105 that produces an audio signal 106. Sound processor 101 processes the audio signal 106 to determine an appropriate pattern of electrical stimulation to apply to the recipient of the cochlear implant.

Generally, the pattern of electrical stimulation is determined in accordance with a set of rules referred to as a sound coding strategy. Typically, the sound processor 101 transmits information specifying the desired stimulation pattern over a transcutaneous radio-frequency (RF) link 103 to an implanted stimulator module 102. The implanted stimulator module 102 generates electrical stimuli and delivers those stimuli to an array of electrodes 104, which are implanted in a recipient's cochlea. Electrically stimulating nerves in a cochlea with a cochlear implant may enable persons with sensorineural hearing loss to perceive sound.

SUMMARY

Current hearing prostheses and other stimulation prostheses suffer from several drawbacks that will be discussed herein. One drawback is that stimulator modules are typically configured with relatively simple state machines, which may limit the stimulator prosthesis to one stimulation strategy and one data protocol that it can process. Thus, configuration data and stimulation data alike are transmitted according to the same protocol. As a result, the stimulation prosthesis either uses a protocol with a high degree of error control, which is inefficient when transmitting stimulation data, or a protocol with a low degree of error control, which is dangerous insofar as the stimulation module could become configured incorrectly. In addition, if a protocol or strategy change is desired, it usually necessitates costly surgery.

To address these shortcomings, the present application discloses a stimulation prosthesis that can operate according to at least two operating states: a configuration state and a stimulation state. The stimulation prosthesis may use a data protocol that is suitable for the current operating state. For example, in one embodiment the stimulation prosthesis uses a communication protocol with a relatively high degree of error control while in the configuration state, and a communication protocol with a relatively low degree of error control while in the stimulation state.

In accordance with another embodiment, the stimulation prosthesis transitions from the stimulation state into the configuration state in order to re-program and operate according to a different stimulation strategy. The stimulation prosthesis may initiate such a transition by temporarily stopping transmission while in the stimulation state. By using the temporary stoppage of transmission as a signal to change operation states, it is less likely that a stimulation module will inadvertently transition into the configuration state and become erroneously programmed.

In accordance with another embodiment, in addition to switching stimulation strategies, the stimulation prosthesis may also switch stimulation data formats to a format that is optimized for the new stimulation strategy.

BRIEF DESCRIPTION OF THE DRAWINGS

FIG. 9 depicts example program code for a Boot ROM routine, in accordance with one embodiment.

FIG. 10 depicts additional example program code for a Boot ROM routine, in accordance with one embodiment.

FIG. 11 depicts example program code for the operation of a stimulation prosthesis in accordance with one embodiment.

FIGS. 12A-G depict example formats of stimulation data, in accordance with several embodiments.

FIGS. 13A-F depict additional example program code for the operation of a stimulation prosthesis in accordance with several embodiments.

FIG. 17 depicts example program code for the operation of a stimulation prosthesis in accordance with one embodiment.

FIG. 18 depicts example program code for the operation of a stimulation prosthesis in accordance with one embodiment.

DETAILED DESCRIPTION

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

Certain aspects of the disclosed systems, methods, and articles of manufacture may be described herein with reference to cochlear implant and acoustic hearing aid embodiments. However, the disclosed systems, methods, and articles of manufacture are not so limited. Many of the disclosed features and functions described with respect to the cochlear implant and acoustic hearing aid embodiments may be equally applicable to other embodiments that may include other types of hearing prostheses, such as, for example, bone anchored hearing aids, direct acoustic cochlear stimulation devices, auditory brain stem implants, or any other type of hearing prosthesis that may be configured to transmit data across a data link.

Moreover, many of the disclosed features and functions may also be applicable to prostheses that use both electrical and acoustic stimulation, sometimes referred to as hybrid devices, and to hearing prostheses that use mechanical stimulation. Further, many of the disclosed features and functions can be applied to any general stimulation prosthesis that includes a data link over which the prosthesis transmits data.

Stimulation Prosthesis Overview

Figure 1:
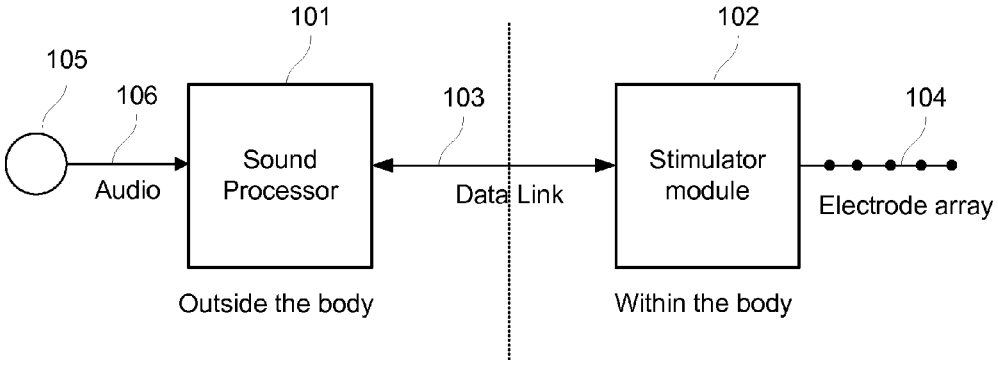
FIG. 1 shows a block diagram of an example cochlear implant system.
Figure 2:
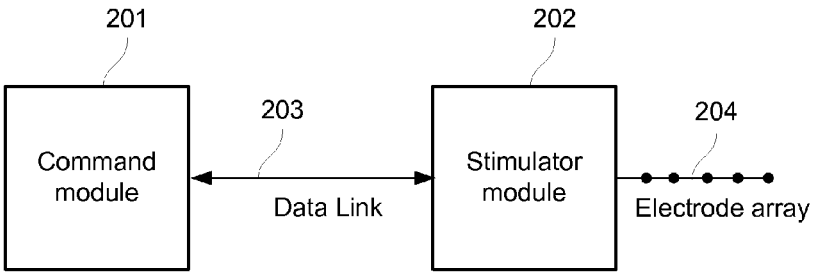
FIG. 2 shows a block diagram of a general stimulation prosthesis, in accordance with one embodiment.

[FIG. 2Error! Reference source not found.] *FIG. 2* depicts a stimulation prosthesis according to an example embodiment. The stimulation prosthesis includes a command module 201, which acts as a stimulation controller, and a stimulator module 202, which generates stimulation pulses for an electrode array 4. The two modules communicate across a data link 203. Typically, data link 203 is a serial, transcutaneous radio frequency (RF) inductive data link. However, in other embodiments, data link 203 is any wired or wireless data link. Stimulation prostheses, such as the prosthesis depicted in FIG. 2 may be configured to apply stimulation to any part of the body, such as the brain, the vestibular system (e.g., to treat balance disorders), the muscular efferent system (e.g., to treat paraplegia), or other afferent nerves (e.g., to restore sensory capabilities).

Most commercial stimulation prostheses, such as cochlear implant hearing prostheses, are configured such that the command module is directly or indirectly attached to the outside of the body and the stimulator module is temporarily or permanently implanted in the body. However, totally-implanted stimulation prosthesis systems are feasible as well (including totally-implanted cochlear implant systems). A totally-implanted system may still be divided into two modules: a sound processor module (or command module) and a stimulator module, in which the two modules communicate across a data link. Despite the fact that both modules are totally-implanted within the prosthesis recipient, such a division between the sound processor module and stimulator module is advantageous because it allows for the sound processor module to be easily replaced. Replacement may be necessary in the event of a fault, a desire to upgrade to a later model, or if the sound processor needs a battery replacement. In contrast, in some embodiments, the stimulator module has many electrical connections to the electrode array, thus making the electrode array somewhat difficult to remove from the prosthesis recipient's body. For example, in cochlear implant embodiments, it can be quite difficult to remove an implanted electrode array from a recipient's cochlea. The disclosed features and functions are applicable to such totally-implanted prosthesis systems.

In at least one hearing prosthesis embodiment, sound processing is carried out by the command module 201. Data sent over data link 203 specifies certain parameters of each individual electrical stimulation pulse that is to be applied by the stimulator module 202 to the electrode array 204. The parameters of each stimulation pulse typically include the amplitude of the current, the pulse waveform shape and timing (e.g., a biphasic pulse with a specified phase width and optionally an inter-phase gap), and the electrodes to be used.

One notable disadvantage of this system is that the pulse rate (i.e., the number of electrical pulses applied to the electrode array per second) is limited by the rate at which data can be sent over the data link 203. Conversely, one notable advantage of this system is that the stimulator module can, in some embodiments, be relatively simple, with little or no internal memory or processing capability.

In some alternate embodiments, all or part of the sound processing function can be performed in the stimulator module instead of the command module. If the sound processing is performed in the stimulator module, then the audio signal itself is typically transmitted across the data link 203. One example configuration utilizes a 16-bit Analog-to-Digital Converter (ADC) at a 16 kHz sampling rate, thereby communicating at a link data rate of 256,000 bits per second (bps). One advantage of such an embodiment is that the pulse rate is no longer limited by the link data rate. One disadvantage of this system, however, is that the stimulator module is usually more complex than normal and consumes more power than normal. As a result, in some embodiments, the sound processing functions are portioned between the command module and the stimulator module at a point where the data rate is relatively low and the memory and processing requirements of the stimulator are relatively modest.

Figure 3:
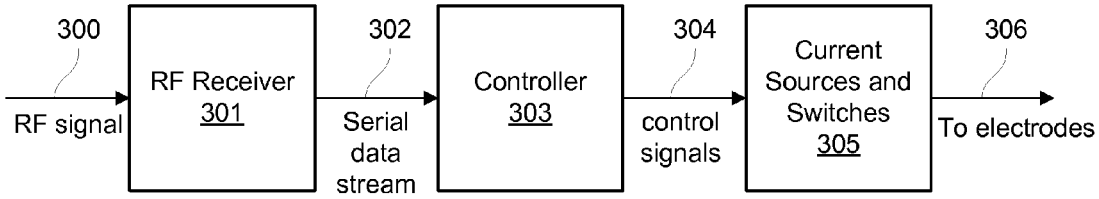
FIG. 3 depicts a block diagram of a stimulator module, in accordance with one embodiment.

FIG. 3 is a block diagram depicting an example configuration of stimulator module, such as stimulator module 202. The RF receiver 301 receives the RF signal 300 from the command module 201 and outputs a stream of data bits 302 to the controller 303. The controller partitions the received data bit stream into distinct words or bit-fields that each have a defined meaning (e.g. an amplitude or electrode number). Then, according to the values of these words, the controller supplies control signals 304 to the current sources and switches 305 to produce stimulation currents 306 with a desired pulse shape, which are in turn applied to electrodes 306. Typically the controller hardware is dependent on the format of data transmitted across data link 203. Thus, to change the data format, one would need to change the hardware of the controller 303.

Data Link Transmission

Referring back to the data link 203, there are many suitable means for the transmission of bits across the data link 203. For example, the link may allow for simultaneous transmission of data in both directions (i.e., to and from the command module 201 and to and from the stimulation module 202). Such transmission is referred to as a "full-duplex" link. Alternatively, transmission to and from the stimulator module 202 may alternate in time. Such transmission is referred to as a "half-duplex" link. The disclosed features and functions are applicable to both types of links.

As is the case with any data transmission system, errors occurring during the transmission of data across data link 203 should be considered and accounted for. One example error control scheme adds error detection bits (e.g., in the form of parity bits or a checksum) to a transmitted message. Adding such bits allows the module receiving the transmission (e.g., the command module or the stimulator module) to detect some (but not all) data transmission errors. For example, a single parity bit allows a single bit error to be detected, but a two-bit error will be undetected. If an error is detected by the receiving module, that module may request a re-transmission. Error detection bits represent an overhead that is an addition to the underlying transmitted message or "payload" data. Thus, error detection bits generally reduce the net data transmission rate. Additionally or alternatively, error correction codes may be used by the receiving module to detect and/or correct some data transmission errors. Generally, error correction codes are associated with a higher overhead requirement than mere error detection bits.

Communication over the data link between the command module and the stimulator module is governed by a protocol, which defines the rules for communication. For example, such rules may include how the data is divided into discrete messages, when each module is expected to send or receive such messages, the format of such messages, and the error control scheme, if any. A further aspect of the protocol is the data format, which defines how data is organized into packets and/or frames that contain groups of bits (referred to as "bit-fields"), and the length and meaning of each such bit-field (sometimes referred to as the "semantics" of the protocol).

Data transmitted from the command module 201 to the stimulator module 202 can be categorized as either configuration data or stimulation data. Configuration data is defined as data that specifies operating parameters of the stimulation prosthesis that are relatively infrequently changed. In a cochlear implant, configuration data refers to those parameters of the stimulation pulses which do not depend on the audio signal. On the other hand, stimulation data is defined as those parameters of the stimulation pulses that dynamically vary according to the audio signal. For example, in the CIS coding strategy for a cochlear implant, the configuration data includes the set of electrodes to be stimulated (some electrodes may be omitted if they are known to be open-circuit or short-circuit, or cause non-auditory sensations), the order of stimulation across the electrodes (base-to-apex or apex-to-base), the stimulation mode (e.g. bipolar or monopolar), the pulse rate, the pulse width to be used for each electrode, and the maximum and minimum current levels to be used with each electrode. These parameters are typically specified by an audiologist when the cochlear implant is fitted to the recipient, and are typically changed no more than a few times a year. Configuration data is sometimes referred to as a "map". Configuration data must be stored somewhere within the stimulation prosthesis. Typically, the command module 201 contains a non-volatile memory to store the configuration data. In some hearing prosthesis embodiments, the stimulator module 202 contains little or no memory, and the full parameters of every pulse are transmitted from the command module 201 to the stimulator module 202. This has the disadvantage of requiring a relatively high data rate. In alternative embodiments, the stimulator module 202 contains volatile memory, and each time the hearing prosthesis is powered, configuration data is transmitted from the command module 201 to the stimulator module 202, and then stored in memory within the stimulator module 202. This has the advantage of requiring a lower data rate during stimulation. For example, in the CIS coding strategy, if the configuration data is transmitted to the stimulator module and stored, then the only stimulation data that needs to be transmitted is the sequence of current levels for each successive pulse. The parameters of the delivered stimulation pulses will depend on both the stored configuration data, and the received stimulation data.

In some hearing prosthesis embodiments, stimulation data has time constraints for its transmission. As described above, the timing of the stimulation pulses delivered to the electrode array 204 is typically dependent upon the timing of the data sent across the data link 203 by command module 201 and subsequently received by stimulator module 202. Changing the timing of the stimulation pulses may degrade the recipient's sound perception. Furthermore, if a data transmission error occurs, there may be little to no time available for the data to be retransmitted.

One option for dealing with errors in received stimulation data is that if the stimulator detects an error, the stimulator module can responsively omit application of a corresponding stimulation pulse. Alternatively, the stimulator module may, in response to detection of stimulation data transmission error, apply a pulse with low or zero current that will not be perceptible to the recipient.

Conversely, configuration data does not necessarily have the same time constraints as stimulation data because it can be sent once when the stimulator initially powers up. Therefore, it is acceptable for the stimulator module to request retransmission of configuration data if an error is detected in the configuration data. As mentioned earlier, some data transmission errors may go undetected. One measure of the seriousness of an undetected data transmission error is how many stimulation pulses are affected by the error. It is good practice to ensure that the transmission of stimulation data is configured such that an undetected error is not persistent. In other words, the transmission of stimulation data is configured such that just a limited number of pulses are affected by any given error. However, an undetected error in configuration data is particularly serious, as it can result in a long-term error, such as incorrect stimulation occurring, in most cases, at least until the next configuration. Therefore, it is important to distinguish between stimulation data and configuration data.

One approach to distinguish between stimulation data and configuration data is to use a header bit in each message. The header bit indicates to the receiving module whether the message contains stimulation or configuration data. However, the header bit is prone to the same errors as the general payload data and as described above, the consequences of an undetected error in this header bit are very severe. For instance, if a stimulation message is mistaken for a configuration message, then the stimulator becomes configured incorrectly. In this case, the command module and the stimulator module will not be on the same page, so to speak, and subsequent stimulation commands sent by the command module will be inappropriately or incorrectly applied by the stimulator module. On the other hand, if a configuration message is mistaken for a stimulation message, then the stimulator module may apply inappropriate or incorrect stimulation in response to receiving the mistaken message while retaining the previous configuration (instead of the intended new configuration). Moreover, all subsequent stimulation may be potentially applied inappropriately or incorrectly.

The seriousness of this hazard has led designers to incorporate additional error control bits within data transmissions so as to provide an acceptably low risk of an undetected error. However, this approach yields a large overhead on stimulation messages, which, in turn, undesirably reduces the rate of data that can be sent over the link.

Sound Coding Strategies

There are many different sound coding strategies for cochlear implants and other hearing and stimulation prostheses. Accordingly, it would be advantageous to enable a single stimulation prosthesis to use a variety of strategies. By way of example, one well-known sound coding strategy is called Continuous Interleaved Sampling (CIS), and is described by Wilson, B., Finley, C., et al. (1991) "Better speech understanding with cochlear implants." Nature 352: 236-238. In this strategy, a filter-bank of a sound processor divides received sound into a number of frequency bands. Each filtering is followed by an envelope detection and then a non-linear instantaneous compression of the envelope signals. The compressed envelope signals are sampled in a fixed order (e.g., high frequency to low frequency) to produce an interleaved pattern of stimulation pulses. These pulses are applied to a corresponding electrode array 204 located in a recipient's cochlea. An active electrode together with the corresponding reference electrode is typically referred to as a "stimulation channel" or simply "channel".

A low data rate can be achieved by sending just the compressed envelopes across the link. The command module and stimulator module can be designed to communicate with a data format optimized for this strategy. Stimulation data sent from such a command module to the stimulator module can be partitioned into packets, in which each packet contains data to produce a single pulse on each stimulation channel. A commonly used set of parameters is 1200 pulses per second on each of 12 channels, with each compressed envelope sample represented with 8 bits. For this case, each packet contains 96 bits (12 words containing 8 bits each) at 1200 packets per second. This data format is referred to as an "amplitude-vector" format and requires a data rate of 115,200 bps, which, as described above, is less than half of the data rate required when directly transmitting the audio across the data link. Other pulse rates, number of channels, and number of bits may be used. In practice, a data packet typically also includes additional bits for error control.

In contrast to the CIS strategy, which repeatedly stimulates all of the chosen electrodes in a fixed order, another strategy, called an "N of M" strategy, applies pulses to a different subset of the electrodes on each scan across the electrode array. Examples of this type of strategy include strategies called "Spectral Peak" (SPEAK), and Advanced Combination Encoder (ACE). The amplitude-vector data format, as described above, can be adapted for this type of strategy, by reserving one special amplitude value (e.g., zero) to indicate that the channel should be skipped. However, this is inefficient.

A typical set of parameters include a selection of 8 electrodes out of 22 electrodes for each scan. Consistent with the example described above with respect to CIS, scans may occur at a rate of 1200 scans per second. In this example, an amplitude-vector packet would contain 176 bits (22×8 bits) to specify 8 pulses. In other words, using the amplitude-vector format with the example N of M sound coding strategy yields an average of one pulse per 22 bits sent across the data link.

A more efficient format is to specify each pulse individually by its channel number and its amplitude. For an example stimulation prostheses that utilizes 22 electrodes, the channel number may be specified with 5 bits and the amplitude may be specified with 8 bits. This yields one pulse per 13 bits sent across the data link. A data format that specifies a channel and amplitude in this format is referred to as a "channel-amplitude" format.

Just as the amplitude-vector format is not particularly efficient when used in combination with an N of M sound coding strategy, the channel-amplitude format is not particularly efficient when used in combination with the CIS strategy. For example, a 12 channel CIS strategy would use 4 bits for the channel number and 8 bits for amplitude. This yields 12 bits per pulse, totaling 144 bits (12×12) per packet. Table 1 illustrates an example comparison of the number of bits used for the amplitude-vector format and the channel-amplitude format for two examples of the CIS and ACE strategies. According to Table 1 and as described above, the amplitude-vector format uses fewer bits in combination with the CIS strategy and the channel-amplitude format uses fewer bits in combination with the ACE strategy.

TABLE 1

| Sound-Coding Strategy | Number of bits for amplitude-vector format | Number of bits for channel-amplitude format |
|---|---|---|
| 12-channel CIS | 12 × 8 = 96 | 12 × 12 = 144 |
| 8 maxima, 22 channel ACE | 22 × 8 = 176 | 8 × 13 = 104 |

In addition, the channel-amplitude format is also suitable for other strategies in which the order of stimulation on the electrodes is not predetermined (as it is with CIS). Such stimulation strategies include the Multi-rate strategy disclosed in U.S. Pat. No. 7,072,717, and the Peak Derived Timing Strategy disclosed in U.S. Pat. No. 7,310,558, in which the order and rate of pulses on each electrode is dependent on the frequency content of the sound. Thus, those skilled in the art will recognize that there is no single data format that is optimal for all strategies.

Controller Design

Figure 4A:
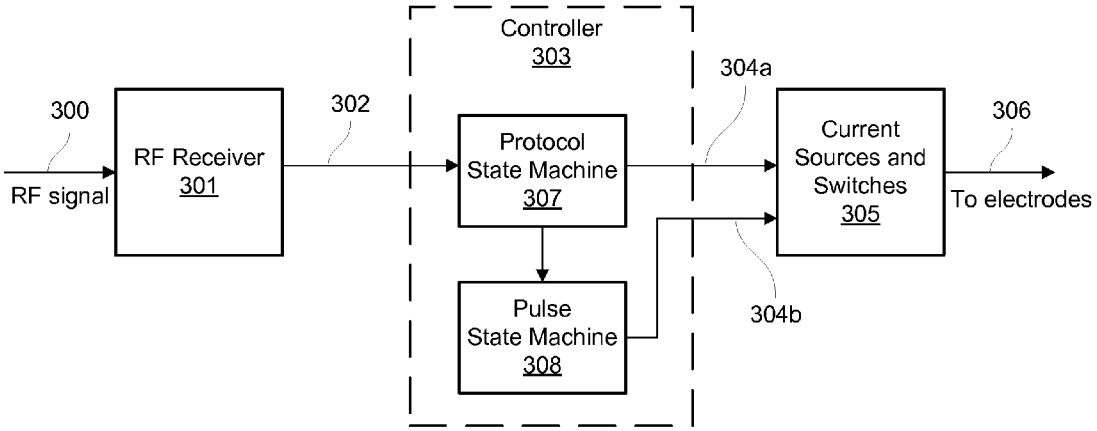
FIGS. 4A-B depict block diagrams of stimulator modules, in accordance with some embodiments.
Figure 4B:
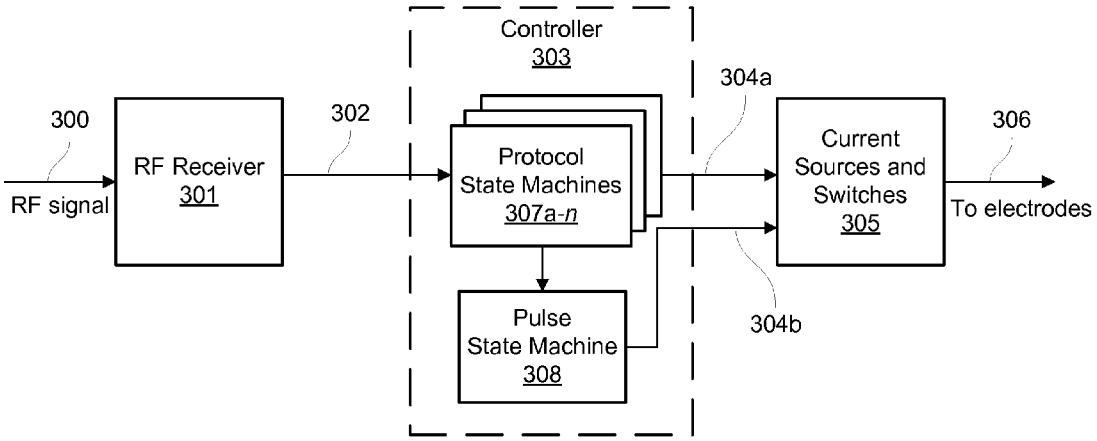

FIGS. 4A and 4B depict the example stimulator module of FIG. 3 but with additional detail shown for the controller 303. In particular, FIG. 4A depicts one example design of a controller that uses two finite state machines: a protocol state machine 307 and a pulse state machine 308. In the example depicted in FIG. 4A, the protocol state machine partitions the data stream 302 into distinct bit-fields in accordance with a predefined serial link data format and writes the bit-fields to appropriate control registers in the pulse state machine 308. In turn, the pulse state machine 308 (sometimes in conjunction with protocol state machine 307) actuates via signal lines 304a and 304b the current sources and switches 305 at appropriate times in order to deliver the desired current waveforms 306. One notable drawback to the controller design depicted by controller 303 is that the protocol state machine 307 is designed for use with just a single protocol.

By way of example, the protocol state machine 307 may include a serial-to-parallel converter (not shown) and associated decoding circuitry (not shown). Such circuitry partitions the serial bit stream from the RF receiver into a succession of 12-bit words. One header bit may be used to distinguish between command words (i.e., configuration data) and amplitude words (i.e., stimulation data). One parity bit is used for error detection. As described above, the drawback to using this type of system is that a data transmission error that causes a bit-flip in both the parity bit and the AMP/CMD bit could go undetected and therefore cause all subsequent stimulation to be incorrect, thus posing a severe hazard.

Table 2 shows an example data format used for each amplitude word in the design of FIG. 4A. The format is similar to the amplitude-vector format described above, which uses 8 bits per pulse. This data format is somewhat less efficient because it uses 11 bits per pulse (not counting the parity bit). An additional overhead of one bit per word (SYNC) is added to allow a variable number of pulses to be specified by each packet. This is not needed for the CIS strategy, as the number of channels is constant and could be configured during initialization. In the CIS strategy, the envelopes are always positive, so a SIGN bit is unnecessary; however, the hardware includes it for use in analog stimulation strategies. Alternatively, the SIGN bit can be configured to be used as a skip bit for N-of-M strategies.

TABLE 2

| Bit | Field | Description |
|---|---|---|
| 11 | PARITY | Odd parity |
| 10 | AMP/CMD | 0 for command word or 1 for amplitude word |
| 9 | SYNC | 1 indicates last word in a packet of amplitude words |
| 8 | SIGN | Sign bit, or skip bit for N of M strategies |
| 0-7 | MAG | 8-bit amplitude magnitude |

These additional bits, which reduce the efficiency of the hearing prosthesis when the CIS sound-coding strategy is used, are seen as a "penalty" for adding some limited flexibility into the data format. This penalty is significant, for example, if the net data rate (excluding error control bits) is 400,000 bps. At this data rate, a data format that uses 8 bits per pulse allows for a total of 50,000 pulses per second (pps), whereas the data format illustrated by Table 2 (11 bits per pulse) allows less than 37,000 pps, a reduction of 27%. Although the hardware configuration depicted in FIG. 4A is somewhat simple, it has the disadvantage of inflexibility because it is configured for use with just the amplitude-vector data format. Consequently, the electrodes are scanned in a predetermined order and it is somewhat inefficient to support an N-of-M strategy. Further, it does not have the flexibility to implement a multi-rate or peak derived timing strategies. Therefore, it would be desirable to implement an improved controller design that handles a multitude of data formats and protocols and can be relatively easily configured.

Described herein are many possible embodiments of a stimulator module that address the shortcomings of the above-described stimulator modules and stimulation prostheses, generally. One such embodiment is depicted by the block diagram of FIG. 4B. Here, the single protocol state machine 307 depicted as part of the controller 303 of FIG. 4A is replaced by a plurality of protocol state machines 307a-n. In particular, there is a separate protocol state machine for each desired protocol to be used with the stimulation prosthesis. However, there are two notable disadvantages associated with such a design. First, a relatively large amount of hardware is used in order to have a separate state machine for each desired protocol. Second, the protocols must be fully determined when the hardware is designed. If a new protocol is developed, then new hardware must be designed, and the new protocol cannot be used with any existing implant recipients.

Figure 5:
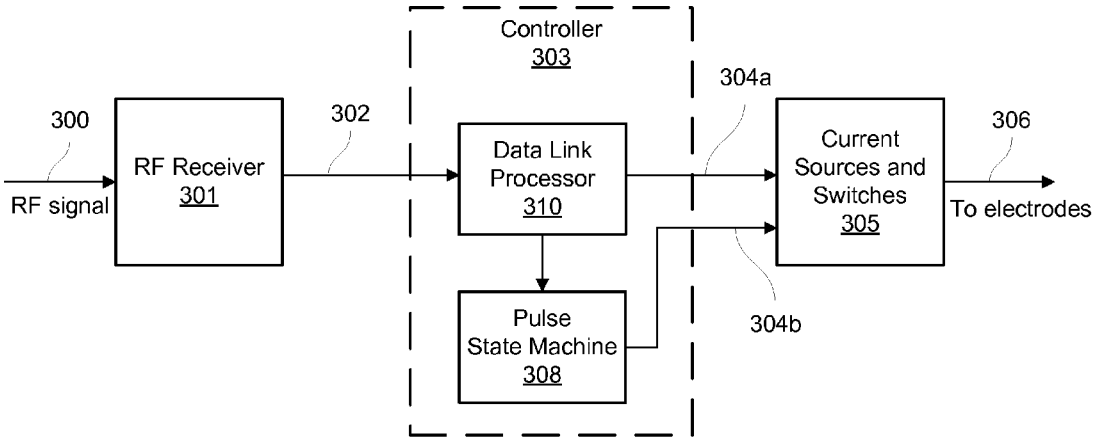
FIG. 5 depicts another block diagram of a stimulator module, in accordance with one embodiment.

FIG. 5 depicts a block diagram of a different controller design, in accordance with one embodiment. In comparison to the controller design of FIG. 4B, the plurality of protocol state machines 307-a-n are replaced in the controller of FIG. 5 by a data link processor 310. In this embodiment, the data link processor 310 executes a program containing instructions that specify how to receive information from the data link and transfer it to the appropriate control registers.

The communication protocol is not determined by the hardware used in the controller 303, which was the case in other controller designs as described above. Rather, the protocol is defined by a software routine running on both the command module and the stimulator module. Therefore, in some embodiments, multiple protocols can be supported with a practical amount of hardware. This represents a substantial change from the other controller designs described above.

Moreover, the communication protocol (and in particular the data format) can be optimised to suit the particular stimulation strategy or sound-coding strategy currently used or desired to be used by the stimulation prosthesis. In the embodiment depicted in FIG. 5, the data link processor 310 is capable of running programs that can be downloaded from the command module. Thus, the command module can load new software into the stimulator module to support a new protocol at any time. In the example controller configurations described above, to change the communication protocol, the implanted stimulator module would have to be removed from the recipient and an entirely new stimulator module built specifically for the desired protocol would have to be implanted Here however, new data formats can be developed in the future to suit new stimulation strategies and they may be used in conjunction with already-implanted stimulator modules configured according to the embodiment depicted in FIG. 5.

Figure 6:
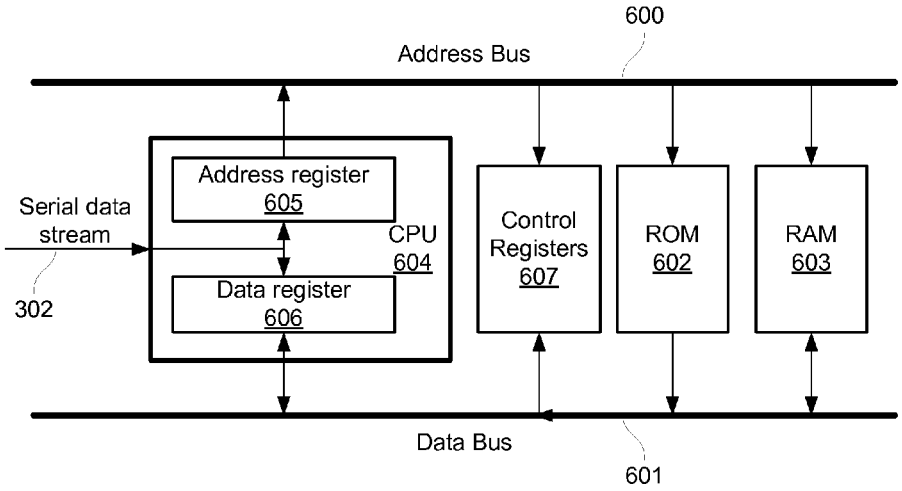
FIG. 6 depicts a block diagram of a data link processor, in accordance with one embodiment.

One example embodiment of the data link processor 310 is shown in FIG. 6. The various blocks are connected by an Address bus 600 and a Data bus 601 (as well as appropriate control signals, which are omitted for brevity's sake). Program instructions are stored in memory, which includes, for example, one or more read-only memory (ROM) modules 602 and one or more random-access memory (RAM) modules 603. The ROM maintains its contents even in the absence of power and typically contains instructions needed to initialize the data link processor 310 after power-up. Such instructions may include instructions for downloading new programs from the command module into the RAM. A central processing unit (CPU) 604 executes instructions, such as those described herein, and accesses an address register 605 and a data register 606. The CPU may also receive bits from the serial data stream 302. Control registers 607 are attached to the address bus 600 and data bus 601 so that they are memory-mapped into CPU address space. The Control registers and the CPU typically provide control signals (not shown) for the pulse state machine 308 and the current sources and switches 305.

The instruction set of the CPU includes instructions for performing such operations as receiving a specified number of bits from the serial data stream 302 and storing them into the address register 605 or data register 606, writing the contents of the data register 606 to a location specified by the address register 605, modifying the address register, and repeating a block of instructions. In addition, the CPU may contain additional registers and the instruction set may include additional instructions that are generally implemented in a CPU, such as arithmetic and logical operations on the registers, and additional flow control instructions, such as tests, branches, calls, and returns.

The data link processor 310 may be based on a general-purpose microprocessor or microcontroller. However, one disadvantage of using a general-purpose microprocessor or microcontroller is that doing so may result in relatively slow operation while consuming a relatively large silicon area and processing power. Furthermore, programs that run on a general-purpose microprocessor or microcontroller may use a relatively large amount of memory. Still further, real-time performance is somewhat difficult to achieve on general-purpose microprocessors or microcontrollers as they typically involve the use of interrupts, which increases the complexity of the software thus further decreasing the reliability of the overall system.

One example embodiment of the stimulator module, which is described further herein, addresses this issue by employing a specialized processor. Such a processor may have a somewhat reduced instruction set optimized for the particular application. This embodiment uses the von Neumann architecture; however, other architectures may also work suitable well.

The specialized processor organizes memory into banks of 32 words. Each word is 8 bits long (i.e., one byte). The first section of memory begins at bank 0 and is configured as ROM. It stores the start-up program instructions, known as the boot ROM program, and allows new programs and data to be loaded into the RAM over the data link.

Table 3 illustrates an example set of registers in accordance with the embodiment depicted in FIGS. 5-6. Other embodiments, however, may use more, fewer, or different registers. The program counter (PC) stores the address of the instruction to be executed. In this example embodiment, the PC is 8 bits wide and allows a maximum program size of 256 bytes. The instruction register (IR) holds the current instruction that is being executed. The frame error (FE) bit indicates the status of the RF receiver. There are five registers that can be manipulated directly, denoted A, B, C, D, E. The accumulator register, denoted A, holds the result of most arithmetic instructions and is a 9-bit register. The bank register, denoted B, is used to select the desired bank of memory. The channel register, denoted C, supplies a 5-bit memory address and selects one byte within the selected bank. The data register, denoted D, is used as a repeat loop counter. The extra register, denoted E, is an additional working register and can also be used as a repeat loop counter. In addition, there is a small hardware stack (S0-S3) that holds program return addresses for subroutine calls in conjunction with a Stack Pointer (SP).

TABLE 3

| Register | Bit width | Description |
|---|---|---|
| PC | 8 | Program Counter |
| IR | 8 | Instruction Register |
| SP | 2 | Stack Pointer |
| FE | 1 | Frame Error |
| A | 9 | Accumulator |
| B | 8 | Bank |
| C | 8 | Channel |
| D | 8 | Data |
| E | 8 | Extra |
| S[0-3] | 8 | Stack (4 deep) |

Timing of the specialized processor is controlled by a master clock, which can be derived from the received RF signal. One instruction cycle consists of two master clock cycles: a fetch cycle and an execute cycle. In the fetch cycle, the program counter (PC) provides the address of an instruction, which is read from memory into the instruction register (IR). During the execute cycle, the instruction is decoded and executed. Some instructions may insert wait cycles to synchronize the operation of the data link processor with the required pulse timing.

Generally, it is desirable to reduce the number of bytes of code and other data that is used to configure the stimulator module. In doing so, this reduces the amount of memory required in the stimulator module and the time taken to transmit the configuration data, thus resulting in an overall improved performance. An example instruction set is depicted in Table 4 and is constructed so that most of the instructions are a single byte. The first column of the table shows a binary representation of the instruction (one or two bytes). Alphabetic characters represent bit-fields within the instruction. The second column shows the name of the OPcode. The third column shows the assembly language syntax of the instruction. And the fourth column provides a brief description of the instruction.

TABLE 4

| Instruction (binary) | OPcode name | Assembly syntax | Description |
|---|---|---|---|
| 0nnkkkkk | LOAD | r[n] = k5 | Load register with immediate 5-bit constant |
| 100nnkkk | RX | r[n]= rx(k) | Receive k bits of RF data into register |
| 10100nnn | A_STORE | r[n]= a | Store A register |
| 10101nnn | A_LOAD | a = r[n] | Load A register |
| 10110nnn | A_ADD | a += r[n] | Add to A register |
| 10111nnn | A_SUB | a −= r[n] | Subtract from A register |
| 11000nnn | CLR | r[n] = 0 | Clear register |
| 11001nnn | INC | r[n]++ | Increment register |
| 11010nnn | DEC | r[n]−− | Decrement register |
| 11011kkk | TX_A | tx_a(k) | Transmit k bits from A register |

TABLE 4-continued

| Instruction (binary) | OPcode name | Assembly syntax | Description |
|---|---|---|---|
| 111000nn kkkkkkkk | LOAD8 | r[n] = k8 | Load register with immediate 8-bit constant |
| 111001nn kkkkkkkk | IF_Z_GOTO | if r[n]== 0 goto label | Branch if register is zero |
| 111010nn kkkkkkkk | IF_P_GOTO | if r[n]!= 0 goto label | Branch if register is positive (non-zero) |
| 11101100 kkkkkkkk | IF_DEC_D_GOTO | if --d goto label | Decrement D and branch if positive (non-zero) |
| 11101101 kkkkkkkk | IF_DEC_E_GOTO | if --e goto label | Decrement E and branch if positive (non-zero) |
| 11101110 kkkkkkkk | GOTO_FG | if !fe goto label | Branch if no frame error |
| 11101111 kkkkkkkk | GOTO_FE | if fe goto label | Branch if frame error |
| 11110000 kkkkkkkk | GOTO | goto label | Unconditional branch |
| 11110001 kkkkkkkk | CALL | call label | Call subroutine |
| 11110010 | CALL_A | call_a | Call subroutine at address specified by A register |
| 11110011 | RET | return | Return from subroutine |
| 11110100 | CLR_FE | fe = 0 | Clear frame error |
| 11110101 | SET_FE | fe = 1 | Set frame error |
| 11110110 | HALVE | a /= 2 | Halve A register |
| 11110111 | ACK | ack | Transmit telemetry acknowledge |
| 11111000 | PULSE | pulse | Start stimulus pulse |
| 11111001 | WAIT | wait | Wait for a frame to be received |

To provide additional detail, the LOAD instruction loads a 5-bit constant into a register. The register is one of A, B, C, or D, as specified by a 2-bit field. The constant is specified by a 5-bit immediate field in the instruction. An analysis of source code reveals that the vast majority of constants are small integers that can fit into 5 bits. In the rare cases that an 8-bit constant is required, the two-byte LOAD8 instruction can be used, in which the constant is stored in the second byte of the instruction.

When, for example, a 13-bit data frame is received, the 13 data bits are written into a serial shift register. The shift register can hold multiple data frames. The RF receiver provides a frame error (FE) bit, which is set high if the received frame was invalid. The FE bit remains high until cleared by the data link processor. The RX instruction reads received data bits from the serial shift register. The number of bits read is in the range 1 to 8, specified by a 3-bit field in the instruction. If the frame error (FE) bit is low, the received bits are written into a destination register (either A, B, C, or D), otherwise the received bits are discarded and the destination register is cleared. The RX instruction inserts wait cycles until the specified number of bits are available before execution continues. The WAIT instruction inserts wait cycles until the next RF frame is received. This allows the program to specify a number of frames to be buffered before processing them.

The TX_A instruction reads data bits from the A register and transmits them back across the data link to the command module. This is sometimes referred to as "back-telemetry" or simply "telemetry." The number of bits transmitted is in the range 1 to 8, specified by a 3-bit field in the instruction. The ACK instruction reads the frame error (FE) bit and transmits it to the external processor. The FE bit is automatically cleared by the TX_A and ACK instructions. The FE bit can also be explicitly controlled by the CLR_FE and SET_FE instructions.

The PULSE instruction requests the pulse state machine 308 to produce a stimulus pulse on the channel specified by the C register with the amplitude specified by the A register. The pulse state machine also provides a status flag indicating whether it is ready to begin a new pulse. If necessary, the PULSE instruction inserts wait cycles to pause operation until the previous pulse is complete before another pulse is triggered. Execution then continues after the wait cycles. In response to the trigger, the pulse state machine 308 outputs the pulse without requiring further intervention from the data link processor 310. The stimulation mode, pulse waveform shape, and timing are determined by values loaded into memory-mapped control registers during the configuration state, which will be described further herein.

The A_STORE and A_LOAD instructions transfer data to and from the A register. The A_ADD and A_SUB instructions perform arithmetic operations with results stored in the A register. In the A_STORE, A_LOAD, A_ADD, and A_SUB instructions, one operand is the A register and the other operand is specified by a 3-bit field. Field values 1 to 4 specify registers B, C, D, E. Field value 0 specifies an operand in memory. The memory address is specified by the B and C registers. This operand is represented in assembly syntax of the form: m[bc]. The CLR, INC, and DEC instructions act on registers A, B, C, D, E.

The GOTO instructions branch to a new program location if a condition is satisfied. The IF_DEC_D_GOTO instruction decrements the D register and then branches if D is not zero. This instruction is used to implement loops that are to be executed a fixed number of times with the D register used as the loop counter. The CALL instruction branches to a subroutine and pushes the return address onto the stack. The RETURN instruction pops the return address from the stack into the program counter. The GOTO and CALL instructions occupy two bytes, with the target address stored in the second byte of the instruction. The CALL_A instruction is used to make indirect calls, where the target address is stored in the A register. It is used in the Boot ROM command handler, to be described later.

In sum, by executing an appropriate sequence of instructions, the received serial bit stream can be partitioned into bit-fields and written to appropriate control registers in order to produce the desired stimulation pulses.

Example Operation

As described above, data transmitted across the data link (i.e., data transmitted between the command module and stimulator module) is generally organized into data frames. In embodiments in which the data link is a transcutaneous RF inductive data link, a data frame contains data and supplies power to the stimulator module. In some embodiments, each frame contains 13 bits of "payload" data together with optional additional bits for synchronization and error-detection purposes, which will not be further described. The number of bits is quantified to give a concrete example; however, the methods and systems described herein can be practiced with frames that contain any suitable number of bits. The 13 bits of data in a frame can be represented as a pair of words (W5, W8), where W5 is a 5-bit word, and W8 is an 8-bit word. For example, (0, 0) or (31, 255) are pairs of words organized in the form of (W5, W8). And as also described above, the stimulator module contains an RF receiver that receives frames and detects errors.

Figure 7A:
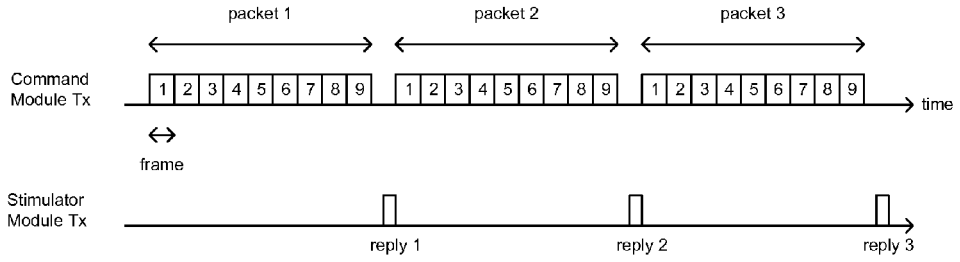
FIG. 7A depicts an example timing diagram for half-duplex communication between a command module and a stimulator module, in accordance with one embodiment.

Furthermore, in some embodiments, data frames are organized into packets. A packet includes one or more frames. The number of frames in a packet is called the packet length. The packet length is not necessarily constant; however, the command module and stimulator module must be configured to both have the same packet length at each moment to avoid errors. An example timing diagram depicting packet transmission in accordance with one embodiment is shown in [7Error! Reference source not found.A] *FIG. 7A*. The top of the diagram indicates when data is transmitted by the command module, and the bottom of the diagram indicates when data is transmitted by the stimulator module. In this embodiment, the packet length is nine and frames are labeled 1 to 9 in each packet. In this embodiment, in normal operation, the stimulator module sends a reply message after reception of each packet.

Figure 7B:
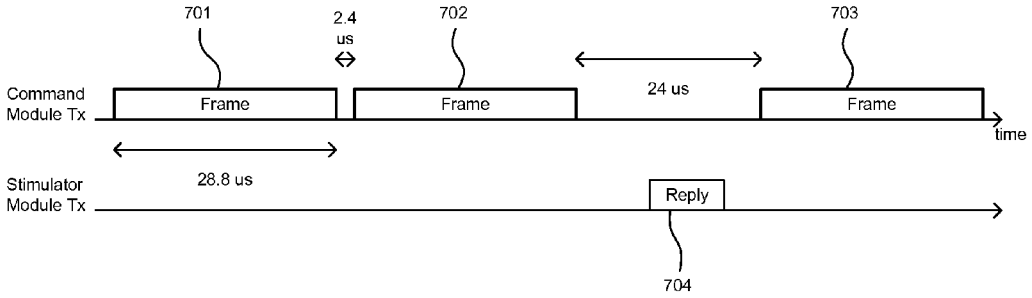
FIG. 7B depicts an example detailed timing diagram for half-duplex communication between a command module and stimulator module, in accordance with one embodiment.

FIG. 7B shows a closer look at the transmission of individual frames in accordance with an example embodiment. In this embodiment, the frame duration is 28.8 microseconds. The protocol utilized in this embodiment is designed so that the command module and stimulator module each know when it is their turn to transmit. For example, frames 701 and 702 are the last two frames in a particular packet, and frame 703 is the first frame of the next packet. Frames within a packet (e.g., frames 701 and 702) are separated by a short gap of 2.4 microseconds in this embodiment. At the end of a packet, the command module waits until it receives the reply 704 from the stimulator module before transmitting the next frame 703. In this embodiment, the resulting gap between packets is 24.0 microseconds. These particular times are disclosed to give a concrete example so that realistic data rates and stimulation rates can be calculated; however, the methods and systems of the present disclosure can be practiced with any suitable frame timing.

Figure 8A:
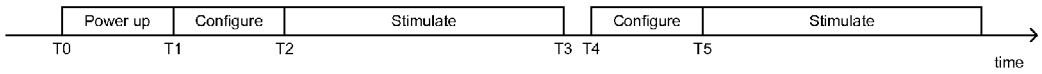
FIG. 8A depicts an example timing diagram for an overall sequence of operation of a stimulation prosthesis, in accordance with one embodiment.
Figure 8B:
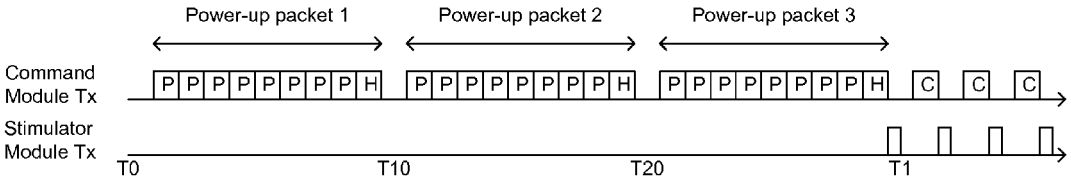
FIG. 8B depicts an example timing diagram for the transmission of individual frames of power-up and configuration states, in accordance with one embodiment.

FIG. 8A shows another timing diagram depicting the overall sequence of operation according to one embodiment. In this embodiment, the stimulator module is initially unpowered at time T0. To power up the stimulator module the command module transmits power-up frames to the stimulator module. FIG. 8B shows more detail of the power-up sequence. The power-up sequence begins at time T0 when the stimulator module is initially unpowered. Each power-up packet consists of a series of power-up frames, denoted P, followed by a command header frame, denoted H. In the embodiment depicted by FIG. 8B, the power-up frame P contains (0, 0), and the command header frame H contains (23, 31), although in other embodiments, the frames may contain different data. After each command header frame H, the command module waits for a reply from the stimulator module. If no reply is received within a predetermined time interval (e.g., illustrated at times T10 and T20), this is taken as an indication that the stimulator module is not yet powered up. Consequently, the command module sends another power-up packet. After a sufficient number of sent power-up packets, the stimulator module will be powered up and will transmit a reply, as shown at time T1. This starts the configuration sequence, denoted by the series of configuration frames C.

Referring back to the overall timing diagram of FIG. 8A, once the stimulator module is powered up at time T1, the stimulator module enters the configuration state. During the configuration state, the command module sends packets to configure the stimulator module. These packets are communicated according to a desired configuration protocol. In accordance with one example embodiment, the configuration protocol is a Stop-and-wait Automatic Repeat reQuest (ARQ) protocol.

For example, when the stimulator module first powers up, it expects a packet length of one so it replies to each frame sent by the stimulator module. A configuration message consists of multiple packets, where each packet contains a single frame. Each configuration message begins with a command header frame H. When the stimulator module receives the command header frame H, the stimulator module replies with an implant type code, which allows the command module to identify the particular model of the stimulator module. The following frames contain the data of the configuration message. Each 13-bit frame contains a 5-bit sequence number and an 8-bit data byte. The sequence number starts at zero, and (in the absence of errors) is incremented by one in each successive frame. The stimulator module maintains its own internal 5-bit frame counter, which is initialized to zero. As each frame is received, the stimulator module compares the received sequence number with its internal frame counter. If they are equal, and the frame is valid, then the frame's data byte is accepted, and the internal frame counter is incremented. If they are not equal, or if the frame was invalid, then the data byte is discarded, and the internal frame counter remains unchanged. In either case, the stimulator module's reply contains the value of its internal frame counter. Thus, the stimulator reply indicates to the command module whether or not the frame was received correctly, and informs the command module which frame of the message should be transmitted next. To further improve efficiency, the reply from the stimulator module does not necessarily need to include all five bits of the internal frame counter. In some cases, a reply consisting of only the two least significant bits is sufficient. With the timing shown in FIG. 7B, a new frame can be transmitted every 52.8 microseconds, yielding a configuration data rate (in the absence of errors) of about 19,000 bytes per second.

Once the stimulator module is configured at time T2, the command module sends a final configuration message that causes the stimulator module to enter the stimulation state. In the stimulation state, the command module transmits packets that contain stimulation data and the stimulator module begins applying stimulation in response to the received stimulation data. These packets are communicated according to a protocol that is optimized for the present stimulation strategy. The protocol used in the stimulation state is usually different from the protocol used during the configuration state.

Continuing, at time T3 the command module makes a determination for one reason or another that it needs to stop the current stimulation and change the configuration of the stimulator module. To do so, the command module temporarily ceases sending packets. The stimulator module expects stimulation packets to be sent continuously and so upon the stimulator module detecting the absence of packets (at time T4), the stimulator module will recognize that this indicates to transition back to the configuration state. The time-out duration must be longer than the usual gap between packets, which in the example embodiment depicted in FIG. 7B was 24 microseconds. However, the time-out duration [Error! Reference source not found.] is preferably not so long as to cause the stimulator module to completely power-down. Once in the configuration state, the command module switches back to the configuration protocol and transmits configuration data to re-configure the stimulator module. Finally, at time T5 the new configuration is complete and stimulation recommences.

In embodiments in which the stimulator module is powered by transmission across the data link, if the data link is temporarily disrupted, then the stimulator module detects the absence of frames and enters the configuration state waiting to be re-configured. The command module detects the absence of replies, pauses in the transmission of packets, and then starts sending power-up packets. If the stimulator module has not yet powered down, it will immediately reply to the power-up packet and begin reconfiguration. If the disruption is sufficiently long (for example, if the external RF transmitter coil was removed), then the stimulator module will power down while it was waiting to be reconfigured. The command module may continue to send power-up packets until the coil is re-attached.

In typical operation, the stimulation prosthesis spends a majority of the time in the stimulation state and re-configuration is infrequent. There could be many reasons for transitioning to the configuration state and re-configuring the stimulator module. For example, a new configuration could be requested manually by the recipient by pressing a button on their processor or remote control (or any other way). Alternatively, the command module could change configuration because it detects a change in the sound environment. Changes in the recipient's sound environment include, for instance, a change from a noisy environment to a quiet environment, a speech-heavy environment to a music-heavy environment, an environment in which sound predominately comes from one direction to an environment in which sound predominately comes from another direction or many directions, or any other suitable sound environment change. Furthermore, the command module could detect that a remaining battery life is low and responsively switch to a configuration that consumes less power. And still further, the command module could switch to another configuration if the current protocol has encountered a high number of errors or the current RF environment is particularly noisy.

In some embodiments, the protocol used for communication during the configuration state has a high level of protection against data transmission errors. Consequently, it has a relatively high overhead and thus, a relatively low payload data transmission rate. On the other hand, in some embodiments, the protocol used for communication during the stimulation state has a lower degree of protection against data transmission errors than the configuration protocol. This is acceptable because the consequences of an undetected error during the stimulation state are not as serious. For example, an error during the stimulation state may cause a finite but small number of incorrect stimulation pulses to be delivered. Because the stimulation protocols have lower degrees of error protection, they have lower overhead and thus, are able to achieve either higher payload data transmission rates or lower power consumption.

In sum, as described herein, the methods and systems of the present disclosure overcome at least some of the limitations of using a single protocol for both configuration and stimulation in which part of the contents of each data packet (e.g. a header bit) determines whether the packet is a configuration message or a stimulation message. This causes added overhead on every packet, and allows the possibility of an undetected error causing the message type to be mistaken. As described, a stimulation prosthesis in accordance with at least one embodiment uses at least two different protocols for communication: a configuration protocol and a stimulation protocol. The message that causes a transition from the configuration state to the stimulation state is sent using the configuration protocol, which has a high degree of error protection. In the stimulation state, the stimulation protocol conveys only stimulation information. The stimulation protocol does not have the capability to convey a configuration message, or a message which would cause the stimulator module to leave the stimulation state. Thus it is not possible for a data transmission error to convert a stimulation message into a configuration message. In such embodiments, the command module causes the stimulator module to leave the stimulation state by temporarily ceasing transmission. Thereby, the risk of data transmission errors causing the message type to be mistaken is drastically reduced, if not eliminated.

Example Data Link Processor Program Code for Power-Up and the Configuration State In some embodiments, the disclosed features and functions of the systems, methods, and algorithms shown and described herein may be implemented as computer program instructions encoded on non-transitory computer readable media in a machine-readable format. Such instructions execute at least one computer process on a computing device. By way of example, the computer readable media may include but is not limited to, a hard disk drive, a Compact Disc (CD), a Digital Video Disk (DVD), a digital tape, flash memory, etc.

The computer program instructions may be, for example, computer executable and/or logic implemented instructions. In some embodiments, a computing device embedded in the command module, stimulator module, or some other module, alone or in combination with one or more other processors associated with the stimulation prosthesis, may be configured to perform various operations, functions, or actions to implement the features and functionality of the disclosed systems and methods based at least in part on the programming instructions.

The following paragraphs describe example assembly-language program code for a data link processor contained in the stimulator module that carries out at least some of the features and functions disclosed herein. Comments start with '#' and extend to the end of the line. Labels are indicated by an identifier followed by ":", and are used as the target of CALL and GOTO instructions.

FIGS. 9 and 10 lists example boot ROM program codes 900 and 1000. In at least one embodiment, upon power-up, the data link processor 310 executes the boot ROM routine Rx_command, as depicted in the program code 900 of FIG. 9. Executing this routine causes the stimulator module to carry out the functionality described above with respect to power-up and operating in the configuration state.

For example, Rx_command receives the first 5 bits of the 13-bit frame into the C register and the second 8 bits into the B register. The routine then compares these received values to the corresponding values of the command header frame H. If there was no match, then it discards the frame, jumps back to the beginning of the routine, and waits to receive the next frame. Thus, during a power-up packet, such as those depicted in FIG. 8B, the stimulator module will ignore all P frames. When a command header frame H is finally received, the stimulator module replies with a 2-bit implant type code. It then receives the following message according to the above-described ARQ protocol.

The routine Rx_frame_count then compares the received sequence number to the internal frame count, which is stored in register E. Rx_frame_count does not return until a valid frame with the expected sequence number has been received. The valid data byte is then ready to be received. The first data byte of a configuration message is received into register A, then used as the program address and jumped to by the CALL_A instruction.

Table 5 shows the structure of an example load memory message, according to one embodiment. This message is used to download data into the RAM of the stimulator module. The data may include configuration data, such as the specific phase width or stimulation mode to be used for subsequent stimulation. Alternatively or additionally, it may include new program code to be executed later. Each row of the table shows the 13-bit data for one frame, divided into a 5-bit word (W5, shown in the first column) and an 8-bit word (W8, shown in the second column). In the table, constants are given in upper case and variable parameters in lower case.

As with typical configuration data messages, the data begins with a command header frame H=(HEADER_W5, HEADER_W8). From there, each frame has a sequence count as W5, and a message byte as W8. The first message byte, denoted LOAD_MEM, is the program address of the Load_mem routine in the Boot ROM, depicted in the program code 1000 of FIG. 10. The data link processor 310 will jump to this routine when it receives this frame. Referring to the Load_mem routine depicted in the program code 1000 of FIG. 10, the data link processor then receives the parameters of the Load_mem routine by repeatedly calling the Rx_frame_count routine to implement the ARQ protocol. The first parameter specifies the memory bank that the data should be loaded into, and is stored into the B register. The second parameter is the offset within the memory bank, and is loaded into the C register. The third parameter is the number of words to be loaded, and is stored in the D register, and used as the loop counter. The body of the loop receives the subsequent data words (of which only the first 3 are shown in Table 5), and stores them into RAM using the A_STORE instruction (i.e., m[bc]=a), which uses the B and C registers to specify the memory address. At the end of the Load_mem routine, execution returns to the Rx_command routine, ready to receive the next configuration message.

TABLE 5

| W5 value | W8 value |
|---|---|
| HEADER_W5 | HEADER_W8 |
| 0 | LOAD_MEM |
| 1 | bank |
| 2 | channel |
| 3 | num_words |
| 4 | word 1 |
| 5 | word 2 |
| 6 | word 3 |

Through these routines, the command module configures the stimulator module by transmitting a succession of appropriate load memory messages. The downloaded data may include a program that performs stimulation according to the desired sound coding strategy. Alternatively, the ROM could contain commonly used stimulation programs. When the configuration is complete, the command module sends a final configuration message with the first message byte equal to the program address of the stimulation routine. The data link processor 310 jumps to that address and starts executing the specified stimulation routine, thus entering the stimulation state.

In some embodiments, each stimulation routine includes a loop. The body of the loop receives one stimulation data packet from the serial data stream, and produces the appropriate stimulation using the PULSE instruction. As mentioned above, to stop the stimulation, for example to reconfigure the stimulator module for a different sound coding strategy, the command module ceases sending RF frames across the data link for a short duration of time (e.g., 100 microseconds). In one embodiment, when the stimulator module detects this time-out, the RF receiver 301 causes a reset of the data link processor 310, which clears the internal registers (including the stack pointer and program counter) and restarts program execution at the beginning of the Boot ROM (e.g., back at the Rx_command routine depicted in program code 900). Thus, the stimulation prosthesis re-enters the configuration state.

Example Data Formats and Data Link Processor Program Code for the Stimulation State The following paragraphs describe several different example stimulation routines and corresponding example computer program code. Each different stimulation routine corresponds to a different data link format. Example data link formats are shown in FIGS. 12A-G.

The ability of a stimulation prosthesis to change the stimulation routine during configuration allows for the use of a data link format optimized for the desired sound coding strategy. In some embodiments, the stimulation routines described do not use the ARQ protocol. Instead, they rely upon the error detection capability inherent in each frame, such as that described above. To reiterate, if an error is detected by the RF Receiver, the frame data will be replaced by zero bits. In most routines, this will then result in minimal amplitude stimulation pulses. At the end of each received packet, the data link processor 310 executes an ACK instruction to provide an acknowledge reply. In some embodiments, such a reply contains a single bit, indicating whether an error has occurred during the reception or processing of the packet, for example, a copy of the frame error (FE) bit. This reply allows the command module to keep track of whether transmission errors are occurring. In some embodiments, the command module modifies the RF transmitter's characteristics in response to the observed error rate.

Many of the stimulation routines have configuration parameters, such as the number of pulses delivered per packet. The configuration parameters are typically calculated by fitting software. In some embodiments, the fitting software runs on a personal computer in a clinic. In other embodiments, the fitting software runs on a remote control device or wireless assistant. The parameters may be selected by an audiologist or other similarly-trained professional or the recipient or a carer. To reduce code size in some embodiments, configuration parameters are stored as immediate constants, most commonly in the five-bit immediate field of a LOAD instruction. The fitting software stores the code for the assembled routine in non-volatile memory in the command module. The command module then downloads the code to the stimulator module during the configuration state.

Because the number of bits in a packet is a multiple of the number of bits in a frame, some data formats contain extra bits, denoted X in FIGS. 12A-G. One option for handling these extra bits is to receive and discard the extra bits. Another option is to use them as additional error detection or checksum bits. For example, the extra bits can be inserted as a header at the start of the packet by the command module. The data link processor 310 can then receive them and check their value.

Example data link processor 310 assembly code for accomplishing this (i.e., the Check_header routine) is depicted by the program code 1100 shown in FIG. 11. This code may be inserted at the beginning of each stimulation routine if the data packet contains extra bits. The configuration parameter num_extra_bits contains the number of extra bits. The configuration parameter expected_header is calculated as the all-ones bit-pattern, (i.e., expected_header=(1<<num_extra_bits)−1). If the extra bits are not high, it indicates an error condition, such as a frame error, or a loss of synchronization (e.g., a lost frame). It could also indicate an error in the command module which is producing incorrectly-formatted packets. In response to this error, Check_header sets the frame error (FE) bit, which causes all subsequent bits of the packet to be received as zero, yielding stimulation pulses of minimal amplitude. Alternatively, it could jump to an error-handling routine that did no stimulation.

Because new stimulation routines can be downloaded into the stimulator module at any time, any of the features and functionality described above can be changed if so desired, without any hardware changes.

The following paragraphs describe example data formats used by the stimulation prosthesis to communicate stimulation data across the data link. Examples of the different data formats are depicted in FIGS. 12A-G and corresponding program code examples for handling the different data formats are depicted in FIGS. 13A-F.

Referring to FIGS. 12A-G, each figure shows a packet made up of one or more 13-bit frames. The top row of each figure shows the frame boundaries, with frames labeled frame 1, frame 2, etc. The middle row of each figure shows the bit-fields within the packet, which are labeled according to their purpose, (e.g., channel 1, amplitude 2, etc.). The bottom row of each figure shows the number of bits in each bit-field. As shown, a bit-field does not necessarily need to be aligned with a frame boundary.

FIG. 12A depicts the channel-amplitude data format, in accordance with one embodiment. This data format is a general purpose format that can be used for just about any sound coding strategy. However, it can be less efficient than some of the more specialized formats described below. FIG. 13A shows an example corresponding program code 1301 for the data link processor 310 referred to as the Stim_chan_amp routine. Each packet consists of a single 13-bit frame and specifies the channel and amplitude of a single pulse. The number of bits for the channel (in this example, 5 bits) and the amplitude (in this example, 8 bits) are specified in the RX instructions. The ACK instruction is used to send a reply to the command module after each PULSE instruction (i.e., after the pulse is started).

Figure 14:
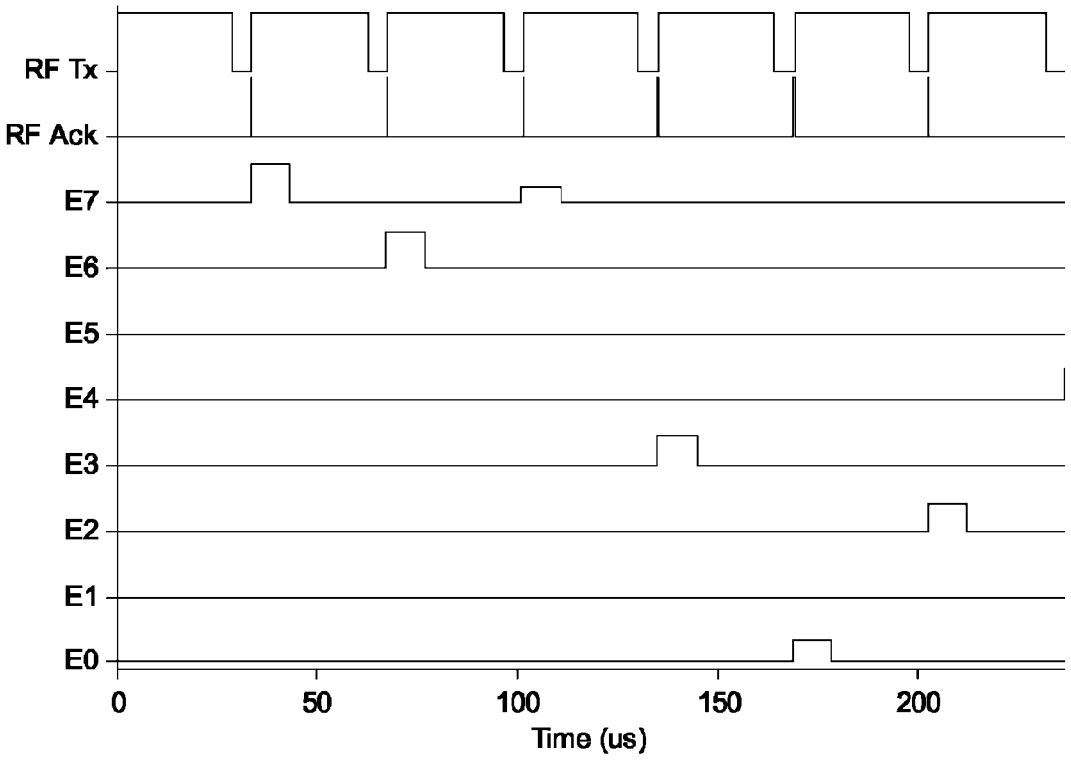
FIG. 14 depicts an example phase diagram, in accordance with one embodiment.

Typically, all pulses have the same duration, which is determined by a control register of the pulse state machine 308 and loaded during the configuration phase. Two different timing schemes can be used, depending on the relationship between the pulse width and the frame period. In the first timing scheme, a stimulation pulse is shorter in duration than one frame period. The pulse rate is determined by the RF frame rate, as illustrated by the timing diagram of FIG. 14. In FIG. 14, the top waveform is the envelope of the RF frame as transmitted by the command module, according to one example embodiment. The next waveform is the RF acknowledge signal transmitted by the stimulator module. The remaining eight waveforms show the electrode currents. To simplify the figure, waveforms are shown for only 8 electrodes (E0-E7), and each pulse has a monophasic waveform. In typical embodiments however, a biphasic waveform would be used, and there could be more or fewer electrodes. In any event, if a half-duplex link with timing given in FIG. 7B is being used, the time used for reply yields a frame rate of about 18,900 frames per second. In other words, this yields a maximum pulse rate of 18,900 pulses per second.

Figure 15:
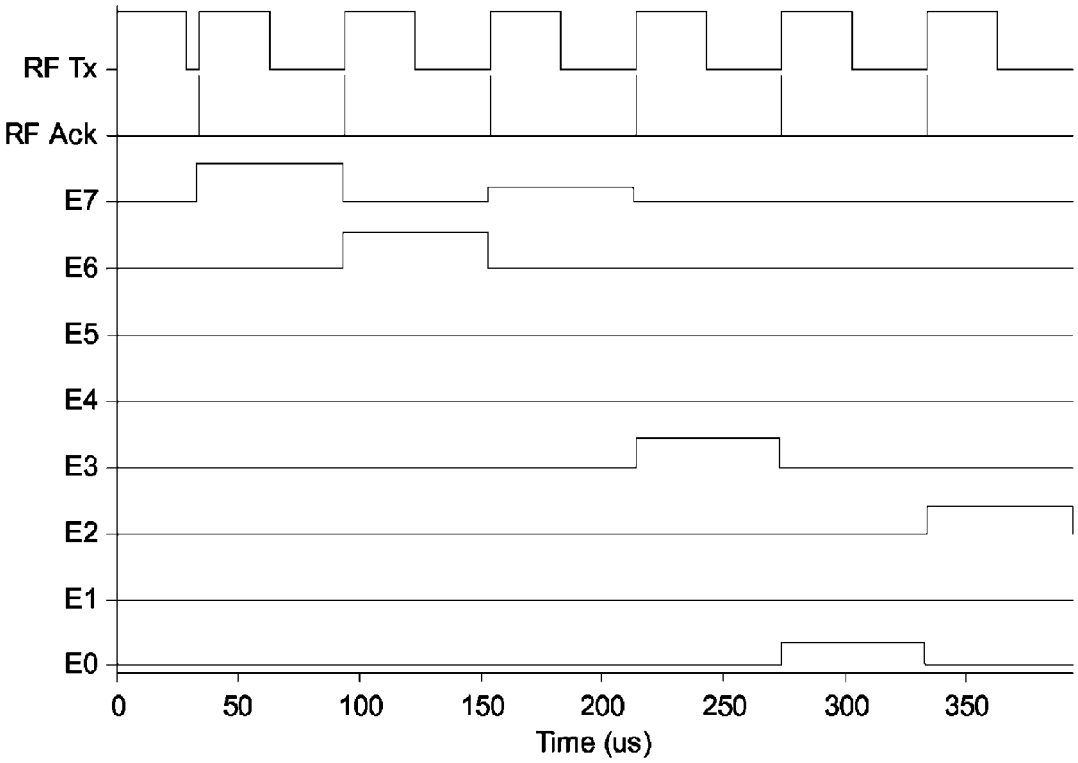
FIG. 15 depicts another example phase diagram, in accordance with one embodiment.

In the second timing scheme, a stimulation pulse is longer in duration than one frame period, and the pulse rate (and the RF frame rate) is determined by the stimulation pulse duration, as illustrated by the timing diagram of FIG. 15. In both timing schemes, the command module and the stimulator module are synchronized by the ACK signal, and the same Stim_chan_amp routine may be used.

In some embodiments, the pulse rate is increased by using a packet containing multiple frames, specifying multiple pulses. The stimulator module sends a single reply at the end of the received packet. One example with six frames per packet is shown in FIG. 12B. With the timing given in FIG. 7B, the duration of a six-frame packet would be about 208.8 microseconds, which yields a pulse rate of about 28,700 pps. FIG. 13B shows an example corresponding program code 1302 used by data link processor 310 referred to as a Stim_chan_amp_group routine. Here, the stimulator module provides a single ACK at the end of the packet. The source code uses the parameter num_pulses to represent the number of pulses in each packet, which acts as the loop counter. Because each pulse is specified independently, this data format can be used with any strategy. If used for the SPEAK or ACE strategies for example, then it is convenient for the number of pulses in each packet to be equal to the number of maxima.

FIG. 12C depicts another example data format referred to as the amplitude-vector data format The example depicted in FIG. 12C is a packet of 5 frames containing data for 8 pulses, which would be suitable for a strategy that used only 8 channels (e.g., 8-channel CIS). Each packet contains one 8-bit amplitude value per channel, plus one extra bit denoted X. FIG. 13C shows an example corresponding program code 1303 used by the data link processor 310 referred to as the Stim_amp_vector routine. Because there is one extra bit, the Check_header code is inserted at the beginning of the routine. The Check_header code would be omitted if there were no extra bits (e.g., if there were 13 channels). The configuration parameter num_channels specifies the number of channels. Pulses are output on consecutive channels, starting at channel 0.

Figure 16:
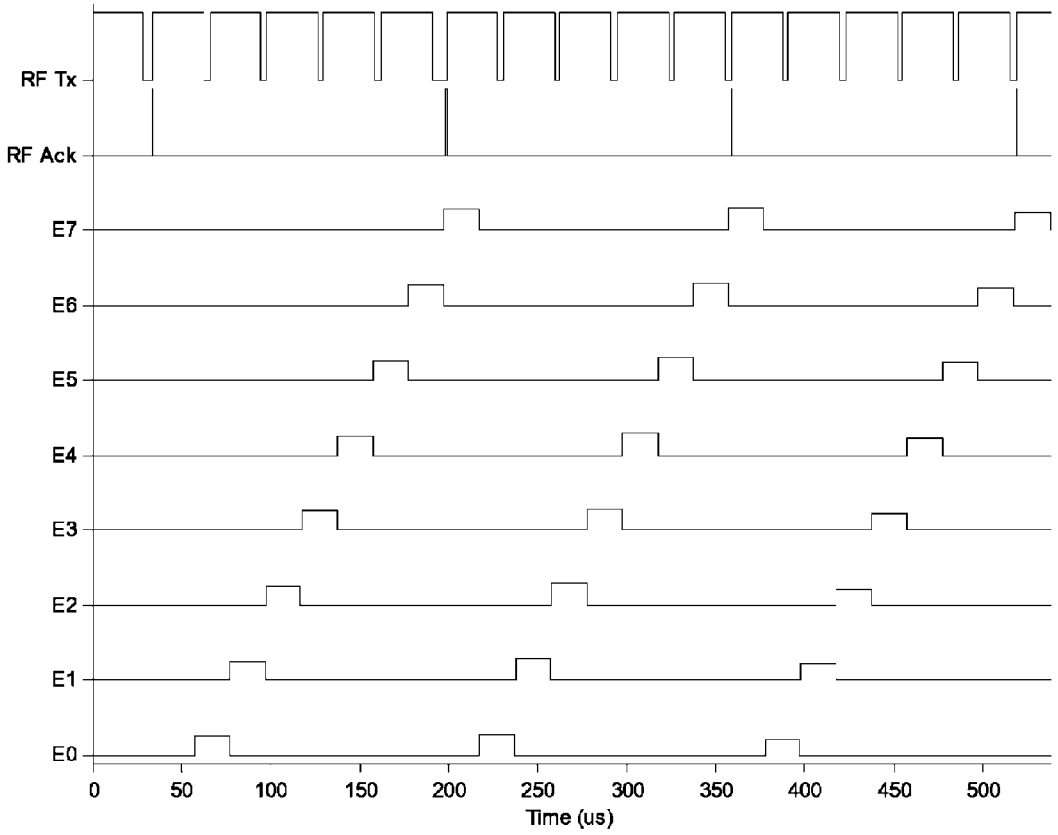
FIG. 16 depicts yet another example phase diagram, in accordance with one embodiment.

In some embodiments, such as the one depicted in FIG. 12C, the amplitude fields are not aligned with the frame boundaries. For example, amplitude 2 is split between frame 1 and frame 2. Thus, amplitude 2 will not be available until frame 2 has been received in its entirety. To address this situation, typically a one-frame delay is introduced (Initial_delay), using the WAIT instruction, before the stimulation loop. FIG. 16 is a timing diagram depicting an example embodiment that uses the one-frame delay. The one-frame delay effectively shifts the packet boundary by one frame so that acknowledgements occur after the first frame of each packet, rather than the last frame. This allows the stimulation loop to remain relatively simple.

For the following data formats, only the main loop will be described; although in practice, the Initial_delay and Check_header code segments are inserted as appropriate.

In some embodiments, the amplitude value is specified by 8 bits (i.e., a value in the range 0 to 255). Typically, the amplitude value is given by the following formula:

$$\text{amplitude}=\text{lower_level}+(\text{upper_level}-\text{lower_level})*\text{magnitude},$$

where lower_level is the lowest amplitude delivered on that channel, and generally corresponds to the recipient's threshold; upper_level is the highest amplitude delivered on that channel, and generally corresponds to the recipient's maximum comfortable level; and magnitude is derived from the amplitude of the signal in the corresponding filter (after non-linear compression) and has a value in the range zero to one. This formula can also be expressed as:

$$\text{amplitude}=\text{lower_level}+\text{height},$$

where height is given by the expression:

$$\text{height}=(\text{upper_level}-\text{lower_level})*\text{magnitude}.$$

The majority of recipients have a range between lower_level and upper_level which is less than 64 discrete values. Thus, a further reduction in data rate can be obtained if the command module specifies a pulse by its height rather than its amplitude.

FIG. 13C shows an example program code 1304 used by the data link processor 310 referred to as the Stim_chan_height routine. This program code implements the channel-height data format. The configuration parameter num_pulses specifies the number of pulses per packet. The configuration parameter num_bits_height specifies the number of bits used to represent the height of each pulse. This is generally fewer than 8, and is typically 6. The configuration parameter num_bits_channel specifies the number of bits used to represent the channel index. The value 4 allows up to 16 channels; the value 5 allows up to 32 channels, and so on. The configuration parameter b_lower_level specifies the memory bank that holds a table containing the value of lower_level for each channel. This table may be downloaded into RAM during configuration. In the inner loop, the C register receives the channel number. The C register is used to index into the lower_level table in the ADD instruction, a +=m[bc], and also specifies the channel for the PULSE instruction (as described in other stimulation routines). If this format is used in conjunction with the SPEAK or ACE strategies for example, then it is convenient for the number of pulses in each packet to be equal to the number of maxima.

A corresponding example packet with num_pulses=8, num_bits_height=6, and num_bits_channel=5 is depicted in FIG. 12D. It occupies 7 frames, and contains 3 extra bits, so the Check_header routine would be inserted after the Stim_chan_height label (not shown in the program code 1304 for brevity). With the timing given in FIG. 7B, [Error! Reference source not found.] the packet duration is about 240.0 microseconds, which yields a pulse rate of about 33,300 pps.

FIG. 13E depicts an example program code 1305 referred to as the Stim_height_vector routine and used by the data link processor 310 in conjunction with a data format called the height-vector format. This format is similar to the amplitude-vector format but replaces amplitude with height. Here, channels are stimulated in consecutive order. An example packet with num_channels=8 and num_bits_height=6 is shown in FIG. 12E. It occupies 4 frames, and contains 4 extra bits, so the Check_header routine would be inserted after the Stim_height_vector label (not shown in the program code 1305 for brevity). With the timing given in FIG. 7B, this configuration has a packet duration of about 146.4 microseconds, which yields a pulse rate of about 54,600 pps.

FIG. 13F depicts an example program code 1306 referred to as the Stim_bit_mask_height routine and used by the data link processor 310 in conjunction with a data format called the bit-mask height format. This format is suitable for N-of-M strategies (e.g., SPEAK and ACE), which, as described above, select a subset of channels for stimulation during each time interval. The configuration parameter num_ channels specifies the total number of channels in the map. The configuration parameter num_pulses specifies the number of pulses in each packet. The configuration parameter num_bits_height specifies the number of bits used to represent the height. A packet with num_channels=22, num_selected=9, and num_bits_height=6 is shown in FIG. 12F. It occupies 6 frames and starts with 2 extra bits. Thus, the Check_header routine would be inserted after the Stim_bit_mask_height label (not shown in the program code 1306 for brevity). The field labeled channel_flags is a bit-mask that specifies which channels are selected for the current scan. It contains one bit per channel, which, according to this example, is 22 bits. The first loop in the program code 1306, labeled Loop_bit_flag, receives the bit-flags one bit at a time and stores them in a buffer in the RAM. The configuration parameter b_bit_flag specifies the memory bank for this buffer. The C register is used to step through the buffer. Register E counts the number of bit-flags that were high. In this configuration, a correctly formatted packet has exactly 9 bits out of 22 high or "set." However, in other configurations, the num_selected parameter may take on other values and consequently, different numbers of bits would be set high in the channel_flags field.

If the received count is correct, the routine proceeds to the Loop_pulse label. Here, the routine iterates through the channels, reading the previously stored bit-flag from the buffer. If the flag is zero, then the present channel is skipped. If the flag is one, then the next height value is received, and a pulse is produced on the present channel. FIG. 12G shows the example packet depicted in FIG. 12F but with actual binary data inserted therein. In this example packet, the 22 channel flags form the binary word '0011011000000110111000'. The flag is 0 for channel 0 and channel 1, so they are skipped. The first pulse occurs on channel 2, with a height of 6. The next pulse occurs on channel 3 with a height of 43. Channel 4 is skipped, and so on. In sum, the channel flags indicate that pulses are produced on channels 2, 3, 5, 6, 13, 14, 16, 17, 18, and 19.

If the received count was incorrect, then the routine jumps to the Bit_flag_error label. In this case, there is no reliable data on which channels should be stimulated, so the remainder of the packet is received and discarded. In one embodiment, a minimal amplitude pulse is produced on the first 9 channels. In another embodiment, no pulses would be produced from such an erroneous packet. With the timing given in FIG. 7B, this configuration has a packet duration of about 208.8 microseconds, which yields a pulse rate of about 43,100 pps.

In some stimulation prosthesis systems, the pulse rate is limited by the data link bit rate because each pulse requires a certain amount of data to be transmitted across the data link. In one embodiment, the data link processor 310 is able to overcome this limitation because it can generate pulses autonomously.

One method of generating autonomous pulses is to use what is referred to as an "interpolation" stimulation technique to produce additional pulses. These additional pulses have an amplitude that is intermediate to the amplitudes that are specified in received data packets. By way of example, FIG. 17 shows a program code 1700 referred to as the Stim_interpolate_vector routine and used by the data link processor 310. This routine uses the height-vector format as previously defined and depicted in FIG. 12E. To reiterate, this is a packet with num_channels=8 and num_bits_height=6. It occupies 4 frames, and contains 4 extra bits, so the Check_header routine would be inserted after the Stim_interpolate_vector label (not shown in program code 1700 for brevity).

The previously-described Stim_height_vector routine (program code 1305 in FIG. 13E) produces 8 pulses during one scan in response to each such packet. In contrast, the Stim_interpolate_vector routine, as depicted in program code 1700, produces 16 pulses in response to each such packet. This amounts to two scans across the electrode array. The Stim_interpolate_vector routine includes two loops. Each iteration of the first loop Loop_rx_and_interpolate receives a height value from the packet and adds the corresponding lower_level to calculate the amplitude of this channel. It then stores the amplitude in a buffer, in the memory bank specified by b_latest_amplitude. It then reads the amplitude of this channel that was derived from the previous packet, which is stored in a second buffer in the memory bank specified by b_previous_amplitude. It then calculates a new amplitude by interpolation between the two amplitudes, according to the expression:

$$\text{amplitude}=(\text{previous_amplitude}+\text{latest_amplitude})/2.$$

A correct 8-bit result is produced because the A register has 9 bits. The routine then outputs a pulse with the interpolated amplitude.

Each iteration of the second loop Loop_output_latest copies a value from the b_latest_amplitude buffer to the b_previous_amplitude buffer, and outputs a pulse having the latest amplitude (i.e., a pulse derived from the data in the latest packet). During configuration, the b_previous_amplitude buffer is initialized to equal the b_lower_level table. With the timing given in FIG. 7B, this configuration has a packet duration of about 146.4 microseconds, which yields a pulse rate of twice that of the Stim_height_vector_routine—about 109,200 pps.

A stimulation strategy that incorporates high-rate "conditioning pulses" may have some benefit. In such a strategy, pulses can be (i) information pulses, which are derived from the audio signal, or (ii) conditioning pulses, which do not carry any information, have fixed amplitude, and are delivered at a high rate. In one embodiment, information pulses and conditioning pulses are delivered to the same electrode in alternating time windows. In some stimulation prosthesis systems, every pulse requires a certain amount of data to be transmitted across the data link, which may limit the rate of the conditioning pulses.

Instead, by way of the data link processor 310 it may be advantageous to generate the conditioning pulses within the stimulator module itself. Therefore, in some embodiments, the data link processor generates such conditioning pulses autonomously. FIG. 18 shows an example program code 1800 referred to as the Stim_height_vector_conditioner routine and used by data link processor 310. It uses the height-vector format defined previously. This routine uses the height-vector format as previously defined and depicted in FIG. 12E. To reiterate, this is a packet with num_channels=8 and num_bits_height=6. It occupies 4 frames, and contains 4 extra bits, so the Check_header routine would be inserted after the Stim_interpolate_vector label (not shown in program code 1800 for brevity).

The first part of the routine contains a nested loop. The inner loop, labeled Loop_conditioner_pulse, outputs one conditioner pulse on each electrode, with amplitudes taken from the configuration table b_condition_level. The configuration parameter num_conditioners specifies the number of times the outer loop, Loop_conditioner_scan, is executed. For example, if num_conditioners is set to two, then there will be two iterations of the outer loop, producing two conditioning scans across the electrode array. The final loop, labeled Information_pulse, produces one information pulse on each electrode.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

[1. A stimulator module comprising:

a receiver configured for receiving data that is transmitted by a command module across a data link, wherein the received data includes stimulation data and configuration data; and a data link processor configured for operating any one of at least two states, wherein:

the at least two states comprise a stimulation state and a configuration state;

operating in the stimulation state comprises generating one or more stimulation pulses by processing the stimulation data according to one of (i) a first stimulation protocol, the first stimulation protocol defining at least a first format of stimulation data for implementing a first stimulation strategy for stimulating one or more channels of the stimulation module, or (ii) a second stimulation protocol, the second stimulation protocol defining at least a second format of stimulation data for implementing a second stimulation strategy for stimulating one or more channels of the stimulation module, wherein the first stimulation strategy and the second stimulation strategy are different stimulation strategies;

processing stimulation data according to the first stimulation strategy comprises the data link processor (a) processing the received data to determine an amplitude for each of M channels of the stimulation module, (b) based on the determined amplitudes, selecting N of the M channels based on an N-of-M stimulation strategy, and (c) for each of the N selected channels, generating one of the one or more stimulation pulses, wherein N and M are positive integers and M is greater than N;

operating in the configuration state comprises processing the configuration data according to a configuration protocol, wherein the configuration data includes instructions for processing the stimulation data according to one of the first stimulation protocol or the second stimulation protocol, and the first stimulation protocol, the second stimulation protocol, and the configuration protocol are different protocols.]

[2. The stimulator module of claim 1, wherein:

the configuration data includes an indication of a conditioning level, the stimulator module is further configured to apply conditioning pulses to at least some stimulation channels between application of successive electric signals to the stimulation channels, and the conditioning pulses have an amplitude about equal to the conditioning level.]

[3. The stimulator module of claim 1, wherein a stimulation rate of the stimulation module depends at least in part on whether the data link processor processes stimulation data according to (a) the first stimulation protocol or (b) the second stimulation protocol.]

[4. The stimulation module of claim 3, wherein the stimulation rate is greater when the data link processor processes stimulation data according to the first stimulation protocol than when the data link processor processes stimulation data according to the second stimulation protocol.]

[5. The stimulator module of claim 1, wherein, for a given set of stimulation data, a number of channels stimulated by the stimulation module depends at least in part on whether the data link processor processes stimulation data according to (a) the first stimulation protocol or (b) the second stimulation protocol.]

[6. The stimulation module of claim 5, wherein the number of channels is greater when the data link processor processes stimulation data according to the first stimulation protocol than when the data link processor processes stimulation data according to the second stimulation protocol.]

[7. The stimulation module of claim 1, wherein the configuration protocol has a higher degree of error control than either the first stimulation protocol or the second stimulation protocol.]

[8. The stimulation module of claim 1, wherein the second stimulation protocol comprises implementing an interpolation technique, and wherein, to implement the interpolation technique, the data link processor is further configured for:

determining a plurality of stimulation values included in a set of processed stimulation data; and determining, for at least one stimulation channel of the stimulation module, an amplitude of an electrical signal by interpolating between any two individual amplitude values in the plurality of amplitude values.]

[9. The stimulation module of claim 1, wherein the N-of-M strategy is an advanced combination encoder strategy for stimulating the one or more channels.]

[10. The stimulation module of claim 1, wherein the N-of-M strategy is a spectral peak strategy for stimulating the one or more channels.]

[11. The stimulation module of claim 1, wherein the data link processor is further configured for, prior to processing the configuration data:

(a) operating the stimulation module in the stimulation state;

(b) determining that the stimulation data is not received within a period of time after receiving previous stimulation data; and (c) responsive to the determining, operating the stimulation module in the configuration state.]

[12. The stimulation module of claim 1, wherein operating in the stimulation state further comprises processing additional stimulation data according to one or more additional stimulation protocols, wherein the one or more additional stimulation protocols differ from each of the first stimulation protocol and the second stimulation protocol.]

*13. A hearing prosthesis, comprising:*

*a stimulator module configured to generate stimulation signals for delivery to a recipient of the hearing prosthesis; and*

*a command module configured to send configuration data and stimulation data to the stimulator module via a data link, and*

*wherein the command module is configured to use a first communication protocol to send the configuration data to the stimulator module and to use a second communication protocol to send the stimulation data to the stimulator module, and wherein the first and second communication protocols are different from one another,*

*wherein the first communication protocol has a higher degree of error control than the second communication protocol.*

*14. The hearing prosthesis of claim 13, wherein the stimulation signals are based on a received audio signal, and wherein the stimulation data comprises parameters of the stimulation signals that vary dynamically according to the received audio signal.*

*15. The hearing prosthesis of claim 13, wherein the stimulation signals are based on a received audio signal, and wherein the configuration data comprises parameters of the stimulation signals that do not vary dynamically according to the received audio signal.*

*16. The hearing prosthesis of claim 13, wherein the data link is a wireless link.*

*17. The hearing prosthesis of claim 16, wherein the data link is a transcutaneous radio frequency (RF) inductive link.*

*18. The hearing prosthesis of claim 13, wherein the command module and the stimulator module are implantable in the recipient.*

*19. The hearing prosthesis of claim 13, wherein the command module is an external component configured to he worn by the recipient.*

*20. A method, comprising:*

*sending, via a data link, configuration data from a command module to a stimulator module of a hearing prosthesis using a first communication protocol; and*

*sending, via the data link, stimulation data from the command module to the stimulator module using a second communication protocol,*

*wherein the first and second communication protocols are different from one another and wherein the first communication protocol has a higher degree of error control than the second communication protocol.*

*21. The method of claim 20, comprising:*

*detecting absence of stimulation data across the data link for a predetermined duration of time; and*

*based on the absence of stimulation data for a predetermined duration of time, determining a reconfiguration of the stimulator module.*

*22. The method of claim 20, wherein the first communication protocol and the second communication protocol have different data formats.*

*23. A method, comprising:*

*sending, via a data link, first stimulation data for a first sound coding strategy from a command module to a stimulator module of a hearing prosthesis using a first communication protocol;*

*generating, at the stimulator module, first stimulation pulses for delivery to a recipient of the hearing prosthesis using the first stimulation data;*

*determining, at the command module, a reconfiguration of the stimulator module for use of a second sound coding strategy that is different from the first sound coding strategy;*

*sending, via the data link, second stimulation data for a second sound coding strategy from the command module to the stimulator module using a second communication protocol that is different from the first communication protocol; and*

*generating, at the stimulator module, second stimulation pulses for delivery to the recipient of the hearing prosthesis using the second stimulation data.*

*24. The method of claim 23, wherein the first communication protocol and the second communication protocol have different data formats.*

*25. The method of claim 23, wherein determining a reconfiguration of the stimulator module comprises:*

*sending, via the data link, configuration data identifying the second sound coding strategy; and*

*initiating the second sound coding strategy at the stimulator module.*

*26. The method of claim 25, wherein prior to receiving the configuration data, the method comprises:*

*detecting absence of first stimulation data across the data link for a predetermined duration of time;*

*in response to detecting the absence of the first stimulation data for the predetermined duration of time, ini-*

*tiating a reset of internal registers in the stimulator module; and initiating a configuration state at the stimulator module.*

*27. The method of claim 25, wherein sending the configuration data identifying the second sound coding strategy comprises:*

*sending the configuration data using a third communication protocol that is different from the first and second communication protocols.*

*28. The method of claim 27, wherein the third communication protocol has a higher degree of error control than either the first or second communication protocols.*

*29. A hearing prosthesis, comprising:*

*a stimulator module configured to generate stimulation signals for delivery to a recipient of the hearing prosthesis, wherein the stimulator module is configured to generate the stimulation signals according to a current sound coding strategy, wherein the current sound coding strategy is selected from among a plurality of different sound coding strategies; and*

*a command module configured to send stimulation data to the stimulator module via a data link, wherein the stimulation data is sent using a communication protocol that varies based on the current sound coding strategy of the stimulator module.*

*30. The hearing prosthesis of claim 29, wherein the plurality of different sound coding strategies comprise at least a first and second sound coding strategies, wherein during a first time period the stimulator module generates first stimulation pulses for delivery to a recipient of the hearing prosthesis using the first sound coding strategy and the during a second time period the stimulator module generates second stimulation pulses for delivery to a recipient of the hearing prosthesis using the second sound coding strategy.*

*31. The hearing prosthesis of claim 30, wherein during the first time period the command module is configured to send first stimulation data to the stimulator module using a first communication protocol, and during the second time period the command module is configured to send second stimulation data to the stimulator module using a second communication protocol that is different from the first communication protocol.*

*32. The hearing prosthesis of claim 31, wherein the first stimulation data and the second stimulation data are each based on received audio signals, and wherein the first stimulation data and the second stimulation data each comprises parameters of the first and second stimulation pulses, respectively, that vary dynamically according to the received audio signals.*

*33. The hearing prosthesis of claim 29, wherein a data format of the communication protocol varies based on the current sound coding strategy of the stimulator module.*

*34. A hearing prosthesis, comprising: a command module; a stimulator module, comprising:*

*a receiver configured to receive data transmitted across a data link from a command module; and*

*a data link processor configured to operate the stimulator module in first and second operating states, wherein the first operating state of the stimulator module is a configuration state in which data received by the receiver via the data link is configuration data and the second operating state of the stimulator module is a stimulation state in which data received by the receiver is stimulation data for use in generating stimulation signals for delivery to a recipient and*

*wherein the configuration data is sent by the command module using a first communication protocol and the stimulation data is sent by the command module using a second communication protocol, and wherein the first communication protocol has a higher degree of error control than the second communication protocol.*

*35. The hearing prosthesis of claim 34, wherein first state of the stimulator module is a first stimulation state in which the stimulator module receives first stimulation data via the data link and generates first stimulation pulses from the first stimulation data according to a first sound coding strategy, and wherein the second state of the stimulator module is a second stimulation state in which the stimulator module receives second stimulation data via the data link and generates second stimulation pulses from the second stimulation data according to a second sound coding strategy.*

*36. The hearing prosthesis of claim 35, wherein the first stimulation data is sent by the command module using a first communication protocol and the second stimulation data is sent by the command module using a second communication protocol that is different from the first communication protocol.*

*37. The hearing prosthesis of claim 36, wherein the first communication protocol and the second communication protocol have different data formats.*

* * * * *